US008058259B2

(12) United States Patent
Thompson et al.

(10) Patent No.: US 8,058,259 B2
(45) Date of Patent: Nov. 15, 2011

(54) SUBSTITUTED 4-{3-[6-AMINO-9-(3,4-DIHYDROXY-TETRAHYDRO-FURAN-2-YL)-9H-PURIN-2-YL]-PROP-2-YNYL}-PIPERIDINE-1-CARBOXYLIC ACID ESTERS AS $A_{2A}R$ AGONISTS

(75) Inventors: Robert Douglas Thompson, Charlottesville, VA (US); Anthony Beauglehole, Charlottesville, VA (US); Frank W. Schmidtmann, Ruckersville, VA (US); Jayson M. Rieger, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 467 days.

(21) Appl. No.: 12/338,599

(22) Filed: Dec. 18, 2008

(65) Prior Publication Data

US 2009/0162282 A1     Jun. 25, 2009

Related U.S. Application Data

(60) Provisional application No. 61/015,415, filed on Dec. 20, 2007.

(51) Int. Cl.
*A01N 43/04*     (2006.01)
*A61K 31/70*     (2006.01)

(52) U.S. Cl. .............. 514/46; 514/42; 514/43; 514/45; 536/27.6

(58) Field of Classification Search .................. None
See application file for complete search history.

(56) References Cited

U.S. PATENT DOCUMENTS

| | | |
|---|---|---|
| 3,892,777 A | 7/1975 | Gruenman et al. |
| 4,012,495 A | 3/1977 | Schmiechen et al. |
| 4,193,926 A | 3/1980 | Schmiechen et al. |
| 4,242,345 A | 12/1980 | Brenner et al. |
| 4,448,721 A | 5/1984 | DeLuca et al. |
| 4,559,157 A | 12/1985 | Smith et al. |
| 4,608,392 A | 8/1986 | Jacquet et al. |
| 4,665,074 A | 5/1987 | Amschler |
| 4,695,660 A | 9/1987 | Otte et al. |
| 4,820,508 A | 4/1989 | Wortzman |
| 4,824,660 A | 4/1989 | Angello et al. |
| 4,879,296 A | 11/1989 | Daluge et al. |
| 4,938,949 A | 7/1990 | Borch et al. |
| 4,956,345 A | 9/1990 | Miyasaka et al. |
| 4,965,271 A | 10/1990 | Mandell et al. |
| 4,968,697 A | 11/1990 | Hutchison |
| 4,992,478 A | 2/1991 | Geria |
| 5,070,877 A | 12/1991 | Mohiuddin et al. |
| 5,096,906 A | 3/1992 | Mandell et al. |
| 5,124,455 A | 6/1992 | Lombardo et al. |
| 5,140,015 A | 8/1992 | Olsson et al. |
| 5,189,027 A | 2/1993 | Miyashita et al. |
| 5,272,153 A | 12/1993 | Mandell et al. |
| 5,278,150 A | 1/1994 | Olsson et al. |
| 5,298,508 A | 3/1994 | Jacobson et al. |
| 5,364,842 A | 11/1994 | Spada et al. |
| 5,561,111 A | 10/1996 | Guerrant et al. |
| 5,561,134 A | 10/1996 | Spada et al. |
| 5,565,462 A | 10/1996 | Eitan et al. |
| 5,593,973 A | 1/1997 | Carter |
| 5,593,975 A | 1/1997 | Cristalli |
| 5,593,976 A | 1/1997 | Mongelli et al. |
| 5,665,754 A | 9/1997 | Feldman et al. |
| 5,668,139 A | 9/1997 | Belardinelli et al. |
| 5,696,254 A | 12/1997 | Mansour et al. |
| 5,731,296 A | 3/1998 | Sollevi |
| 5,756,706 A | 5/1998 | Mansour et al. |
| 5,776,940 A | 7/1998 | Daluge et al. |
| 5,854,081 A | 12/1998 | Linden et al. |
| 5,877,180 A | 3/1999 | Linden et al. |
| 5,877,190 A | 3/1999 | Dhainaut et al. |
| 5,932,558 A | 8/1999 | Cronstein et al. |
| 5,998,386 A | 12/1999 | Feldman |
| 6,004,945 A | 12/1999 | Fukunaga |
| RE36,494 E | 1/2000 | Olsson et al. |
| 6,020,321 A | 2/2000 | Cronstein et al. |
| 6,020,339 A | 2/2000 | Perrier et al. |
| 6,034,089 A | 3/2000 | Han et al. |
| 6,060,481 A | 5/2000 | LaNoue et al. |
| 6,117,878 A | 9/2000 | Linden et al. |
| 6,232,297 B1 | 5/2001 | Linden et al. |
| 6,303,619 B1 | 10/2001 | Linden et al. |
| 6,322,771 B1 | 11/2001 | Linden et al. |
| 6,326,359 B1 | 12/2001 | Monaghan et al. |
| 6,332,771 B1 | 12/2001 | Adams et al. |
| 6,339,072 B2 | 1/2002 | Martin et al. |
| 6,350,735 B1 | 2/2002 | Monaghan |
| 6,387,889 B1 | 5/2002 | Endo et al. |
| 6,407,076 B1 | 6/2002 | Box et al. |
| 6,448,235 B1 | 9/2002 | Linden et al. |
| 6,455,510 B1 | 9/2002 | Charles et al. |
| 6,514,949 B1 | 2/2003 | Linden et al. |
| 6,525,032 B2 | 2/2003 | Mantrell et al. |
| 6,531,457 B2 | 3/2003 | Linden et al. |
| 6,545,002 B1 | 4/2003 | Linden et al. |
| 6,624,158 B2 | 9/2003 | Mantell et al. |
| 6,670,334 B2 | 12/2003 | Linden |
| 6,936,596 B2 | 8/2005 | Konno et al. |
| 7,214,665 B2 | 5/2007 | Linden et al. |
| 7,226,913 B2 | 6/2007 | Linden et al. |
| 7,307,079 B2 | 12/2007 | Den Hartog et al. |

(Continued)

FOREIGN PATENT DOCUMENTS

EP     0488331 A1     6/1992

(Continued)

OTHER PUBLICATIONS

"U.S. Appl. No. 11/673,360, Response filed Mar. 25, 2011 to Non Final Office Action mailed Nov. 26, 2010", 27 pgs.

(Continued)

*Primary Examiner* — Traviss C McIntosh, III
(74) *Attorney, Agent, or Firm* — Schwegman, Lundberg & Woessner, P.A.

(57) ABSTRACT

The present invention provides substituted 4-{3-[6-amino-9-(3,4-dihydroxy-tetrahydro-furan-2-yl)-9H-purin-2-yl]-prop-2-ynyl}-piperidine-1-carboxylic acid esters and pharmaceutical compositions containing the same that are selective agonists of $A_{2A}$ adenosine receptors (ARs). These compounds and compositions are useful as pharmaceutical agents.

19 Claims, No Drawings

U.S. PATENT DOCUMENTS

| | | | |
|---|---|---|---|
| 7,378,400 B2 | 5/2008 | Rieger et al. | |
| 7,396,825 B2 | 7/2008 | Okusa et al. | |
| 7,427,606 B2 | 9/2008 | Linden et al. | |
| 7,442,687 B2 | 10/2008 | Rieger et al. | |
| 7,553,823 B2 | 6/2009 | Zablocki et al. | |
| 7,576,069 B2 * | 8/2009 | Rieger et al. | 514/46 |
| 7,589,076 B2 * | 9/2009 | Rieger et al. | 514/46 |
| 7,605,143 B2 | 10/2009 | Rieger et al. | |
| 7,737,127 B2 | 6/2010 | Linden et al. | |
| 7,875,595 B2 | 1/2011 | Rieger et al. | |
| 7,888,329 B2 * | 2/2011 | Rieger et al. | 514/46 |
| 2001/0027185 A1 | 10/2001 | Linden et al. | |
| 2002/0032168 A1 | 3/2002 | Mantrell et al. | |
| 2002/0058641 A1 | 5/2002 | Mantell et al. | |
| 2002/0072597 A1 | 6/2002 | Mantell et al. | |
| 2003/0013675 A1 | 1/2003 | Yeadon et al. | |
| 2003/0162742 A1 | 8/2003 | Linden et al. | |
| 2003/0186925 A1 | 10/2003 | Palmer et al. | |
| 2003/0186926 A1 | 10/2003 | Linden et al. | |
| 2004/0229246 A1 | 11/2004 | Fishman et al. | |
| 2005/0004221 A1 | 1/2005 | Hildebrand et al. | |
| 2005/0020532 A1 | 1/2005 | Elzein et al. | |
| 2005/0182018 A1 | 8/2005 | Linden et al. | |
| 2005/0261236 A1 | 11/2005 | Okusa et al. | |
| 2005/0282831 A1 | 12/2005 | Beauglehole et al. | |
| 2006/0030889 A1 | 2/2006 | Ben-Haim et al. | |
| 2006/0040888 A1 | 2/2006 | Rieger et al. | |
| 2006/0040889 A1 | 2/2006 | Rieger et al. | |
| 2006/0052298 A1 | 3/2006 | Guerrant et al. | |
| 2006/0100169 A1 | 5/2006 | Rieger et al. | |
| 2006/0128652 A1 | 6/2006 | Jagtap et al. | |
| 2006/0217343 A1 | 9/2006 | Rieger et al. | |
| 2007/0027073 A1 | 2/2007 | Rubinstein et al. | |
| 2007/0032450 A1 | 2/2007 | Rieger | |
| 2007/0232559 A1 | 10/2007 | Linden et al. | |
| 2007/0265440 A1 | 11/2007 | Linden et al. | |
| 2008/0009460 A1 | 1/2008 | Linden et al. | |
| 2008/0027022 A1 | 1/2008 | Linden et al. | |
| 2008/0064653 A1 | 3/2008 | Li et al. | |
| 2008/0214581 A1 | 9/2008 | Allen et al. | |
| 2008/0262001 A1 | 10/2008 | Kranenburg et al. | |
| 2008/0312160 A1 | 12/2008 | Guerrant et al. | |
| 2009/0012035 A1 | 1/2009 | Jacobson et al. | |
| 2009/0081764 A1 | 3/2009 | Pausch et al. | |
| 2009/0118309 A1 | 5/2009 | Beauglehole et al. | |
| 2009/0123510 A1 | 5/2009 | Cronstein et al. | |
| 2009/0162292 A1 | 6/2009 | Thompson et al. | |
| 2009/0170803 A1 | 7/2009 | Linden et al. | |
| 2009/0181920 A1 | 7/2009 | Watkins et al. | |
| 2009/0253647 A1 | 10/2009 | Rieger et al. | |
| 2009/0280059 A1 | 11/2009 | Rieger et al. | |
| 2009/0298788 A1 | 12/2009 | Rieger et al. | |
| 2009/0325967 A1 | 12/2009 | Fairhurst et al. | |
| 2010/0152127 A1 | 6/2010 | Linden et al. | |
| 2010/0166698 A1 | 7/2010 | Rieger | |

FOREIGN PATENT DOCUMENTS

| | | | |
|---|---|---|---|
| EP | 0488336 A1 | 6/1992 |
| EP | 0488336 B1 | 5/1995 |
| EP | 0700908 A1 | 3/1996 |
| EP | 1110554 A1 | 6/2001 |
| EP | 1150991 B1 | 11/2001 |
| EP | 1194440 A2 | 4/2002 |
| EP | 1194440 B1 | 2/2005 |
| HU | 174074 | 10/1979 |
| HU | 0200224 A | 6/2002 |
| IL | 144188 B | 12/2008 |
| JP | 6299330 A | 5/1987 |
| JP | 06299335 A | 5/1987 |
| JP | 03287537 A | 12/1991 |
| JP | 59197 A | 1/1993 |
| JP | 59198 A | 1/1993 |
| JP | 05025195 A | 2/1993 |
| JP | 05163294 A2 | 6/1993 |
| JP | 07508718 | 9/1995 |
| JP | 11335302 A | 12/1999 |
| JP | 20007695 A | 1/2000 |
| JP | 2002536300 | 10/2002 |
| NZ | 530976 | 7/2005 |
| WO | WO-9005526 A1 | 5/1990 |
| WO | WO-9015812 A1 | 12/1990 |
| WO | WO-9109864 A1 | 7/1991 |
| WO | WO-9322328 A1 | 11/1993 |
| WO | WO-9602553 A2 | 2/1996 |
| WO | WO-9604280 A1 | 2/1996 |
| WO | WO-9847509 A1 | 10/1998 |
| WO | WO-9852611 A1 | 11/1998 |
| WO | WO-9857651 A1 | 12/1998 |
| WO | WO-9857661 A1 | 12/1998 |
| WO | WO-9934804 A1 | 7/1999 |
| WO | WO-9938877 A2 | 8/1999 |
| WO | WO-9941267 A1 | 8/1999 |
| WO | WO-9962518 A1 | 12/1999 |
| WO | WO-9963938 A2 | 12/1999 |
| WO | WO-9967263 A1 | 12/1999 |
| WO | WO-9967264 A1 | 12/1999 |
| WO | WO-9967265 A1 | 12/1999 |
| WO | WO-9967266 A1 | 12/1999 |
| WO | WO-0012098 A1 | 3/2000 |
| WO | WO-0023457 A1 | 4/2000 |
| WO | WO-0044763 A2 | 8/2000 |
| WO | WO-0044763 A3 | 8/2000 |
| WO | WO-0072799 A2 | 12/2000 |
| WO | WO-0078774 A2 | 12/2000 |
| WO | WO-0078774 A3 | 12/2000 |
| WO | WO-0078777 A1 | 12/2000 |
| WO | WO-0078779 A2 | 12/2000 |
| WO | WO-0194368 A1 | 12/2001 |
| WO | WO-0209701 A1 | 2/2002 |
| WO | WO-0222630 A1 | 3/2002 |
| WO | WO-02096462 A1 | 12/2002 |
| WO | WO-03004137 A1 | 1/2003 |
| WO | WO-03014137 A1 | 2/2003 |
| WO | WO-03029264 A2 | 4/2003 |
| WO | WO-03029264 A3 | 4/2003 |
| WO | WO-03086408 A1 | 10/2003 |
| WO | WO-03090733 A1 | 11/2003 |
| WO | WO-2005084653 A2 | 9/2005 |
| WO | WO-2005097140 A2 | 10/2005 |
| WO | WO-2005107463 A1 | 11/2005 |
| WO | WO-2006015357 A2 | 2/2006 |
| WO | WO-2006015357 A3 | 2/2006 |
| WO | WO-2006023272 A1 | 3/2006 |
| WO | WO-2006028618 A1 | 3/2006 |
| WO | WO-2007092936 A2 | 8/2007 |
| WO | WO-2007092936 A3 | 8/2007 |
| WO | WO-2007092936 C2 | 8/2007 |
| WO | WO-2007120972 A2 | 10/2007 |
| WO | WO-2007120972 A3 | 12/2007 |
| WO | WO-2008124150 A1 | 10/2008 |

OTHER PUBLICATIONS

"U.S. Appl. No. 11/765,320, Response filed Jan. 20, 2011 to Non Final Office Action mailed Aug. 20, 2010", 22 pgs.

"U.S. Appl. No. 12/487,235, Notice of Allowance mailed Mar. 25, 2011", 7 pgs.

"U.S. Appl. No. 12/487,235, Response filed Feb. 18, 2011 to Final Office Action mailed Sep. 20, 2010", 11 pgs.

"U.S. Appl. No. 12/712,022, Non Final Office Action mailed Mar. 23, 2011", 53 pgs.

"U.S. Appl. No. 12/712,022, Response filed Feb. 7, 2011 to Non Final Office Action mailed Nov. 9, 2010", 27 pgs.

"U.S. Appl. No. 13/027,901, Non Final Office Action mailed Mar. 31, 2011", 15 pgs.

"Canadian Application Serial No. 2460911, Notice of Allowance mailed Dec. 21, 2010", 1 pg.

"European Application Serial No. 02800432.3, Office Action mailed Dec. 29, 2010", 3 pgs.

"European Application Serial No. 02800432.3, Response filed Mar. 17, 2011 to Non Final Office Action mailed Dec. 29, 2010", 40.

"European Application Serial No. 05756108.6, Office Action mailed Feb. 3, 2011", 7 pgs.

"European Application Serial No. 05803845.6, Response filed Feb. 9, 2011 to Non Final Office Action mailed Oct. 18, 2010", 3 pgs.

"International Application Serial No. PCT/US09/30565, International Search Report and Written Opinion mailed Apr. 6, 2009", 7 pgs.

"Japanese Application Serial No. 2001-504969, Response filed Jan. 7, 2011 to Office Action mailed Jul. 1, 2010", 3 pgs.

"Japanese Application Serial No. 2007-511486, Office Action mailed Feb. 8, 2011", 4 pgs.

Clerici, C., et al., "Effect of Intraduodenal Administrative of 23-Methyl-UDCA Diastereoisomers on Bile Flow in Hamsters", Digestive Diseases and Sciences, vol. 37, No. 5, (May 1992), 791-798.

Goodwin, Jay T, et al., "Physicochemical Determinants of Passive Membrane Permeability: Role of Solute Hydrogen-Bonding Potential and Volume", J Med Chem, 44, (2001), 3721-3729.

Kerns, Edward, et al., "Drug-Like Properties: Concepts, Structure Design and Methods: From ADME to Toxicity Optimization", Elsevier, (2008), 92:96.

Nogrady, Thomas, et al., "Medicinal Chemistry: A Molecular and Biochemical Approach", Oxford University Press, 3rd Edition, (2005), 135.

Okusa, M. D, et al., "Enhanced protection from renal ischemia-reperfusion injury with A(2A)-adenosine receptor activation and PDE 4 inhibition.", Kidney Int., 59(6), (Jun. 2001), 2114-25.

Okusa, M. D, et al., "Selective A2A adenosine receptor activation reduces ischemia-reperfusion injury in rat kidney", Am J Physiol., 277(3 Pt 2), (Sep. 1999), F404-12.

Remuzon, Philippe, et al., "Fluoronaphthyridines as Antibacterial Agents. 6. Synthesis and Structure-Activity Relationships of New Chiral 7-(1-, 3-, 4-, and 6-Methyl-2, 5-Diazabicyclo [2.2.1] heptan-2-yl-1-(1,1-dimethylethyl)-6-fluoro-1,4-di-hydro-4-oxo1, 8-naphthyridine-3- . . . ", J Med Chem, 35, (1992), 2898-2909.

Shikata, Kemichi, et al., "Therapies for diabetic nephropathy", Journal of Clinical and Experimental Medicine: 209(1), (Apr. 2004), 54-59.

Silverman, R., et al., "The Organic Chemistry of Drug Design and Drug Action", Academic Press, (1992), 16-17.

"", The Merck Manual of Diagnosis and Therapy, Beers, M.A., et al. (eds.), Merck and Company, (Jan., 1999), 924-925.

""STN Database Descriptions"", Chemical Abstracts Catalog, (2006), p. 52.

"U.S. Appl. No. 08/272,821, Non Final Office Action mailed Mar. 9, 1998", 6 pgs.

"U.S. Appl. No. 08/272,821, Notice of Allowance mailed Aug. 5, 1998", 4 pgs.

"U.S. Appl. No. 08/272,821, Preliminary Amendment filed Jun. 20, 1997", 5 pgs.

"U.S. Appl. No. 08/272,821, Response filed Jun. 9, 2008 to Non Final Office Action mailed Mar. 9, 2008", 8 pgs.

"U.S. Appl. No. 08/272,821, Response filed Nov. 3, 1997 to Restriction Requirement mailed Oct. 2, 1997", 5 pgs.

"U.S. Appl. No. 08/272,821, Restriction Requirement mailed Oct. 2, 1997", 5 pgs.

"U.S. Appl. No. 09/003,930, Final Office Action mailed Aug. 6, 1999", 6 pgs.

"U.S. Appl. No. 09/003,930, Non-Final Office Action mailed Nov. 4, 1998", 7 pgs.

"U.S. Appl. No. 09/003,930, Preliminary Amendment filed Feb. 8, 1999", 5 pgs.

"U.S. Appl. No. 09/003,930, Response filed May 4, 1999 to Non-Final Office Action mailed Nov. 4, 1998", 12 pgs.

"U.S. Appl. No. 09/003,930, Response filed Nov. 4, 1999 to Final Office Action mailed Aug. 6, 1999", 10 pgs.

"U.S. Appl. No. 09/320,769, Non Final office action mailed Jul. 18, 2000", 5 pgs.

"U.S. Appl. No. 09/333,387, Non-Final Office Action mailed Jul. 13, 2000", 5 pgs.

"U.S. Appl. No. 09/333,387, Notice of Allowance mailed Aug. 25, 2000", 2 pgs.

"U.S. Appl. No. 09/333,387, Response filed Aug. 28, 2000 to Non-Final Office Action mailed Jul. 13, 2000", 2 pgs.

"U.S. Appl. No. 09/333,387, Supplemental Amendment filed Aug. 28, 2000", 2 pgs.

"U.S. Appl. No. 09/333,387, Supplemental Notice of Allowability mailed Mar. 7, 2001", 4 pgs.

"U.S. Appl. No. 09/336,198, Non Final Office Action mailed Mar. 8, 2001", 7 pgs.

"U.S. Appl. No. 09/336,198, Notice of allowance mailed Jun. 25, 2001", 4 pgs.

"U.S. Appl. No. 09/336,198, Response filed Jun. 8, 2001 to Non Final office action mailed Mar. 8, 2001", 4 pgs.

"U.S. Appl. No. 09/543,385, Notice of Allowance mailed Mar. 25, 2002", 5 pgs.

"U.S. Appl. No. 09/543,385, Notice of Allowance mailed Sep. 24, 2001", 5 pgs.

"U.S. Appl. No. 09/543,385, Preliminary Amendment filed Apr. 4, 2000", 2 pgs.

"U.S. Appl. No. 09/543,385, Response filed Jun. 29, 2001 to Restriction Requirement mailed May 29, 2001", 2 pgs.

"U.S. Appl. No. 09/543,385, Restriction Requirement mailed May 29, 2001", 3 pgs.

"U.S. Appl. No. 09/543,385, Supplemental Preliminary Amendment filed Aug. 31, 2000", 6 pgs.

"U.S. Appl. No. 09/634,407, Non Final office action mailed Sep. 25, 2001", 21 pgs.

"U.S. Appl. No. 09/634,407, Notice of allowance mailed Sep. 4, 2002", 10 pgs.

"U.S. Appl. No. 09/634,407, Response filed Feb. 26, 2002 to Non Final office action mailed Sep. 25, 2001", 8 pgs.

"U.S. Appl. No. 09/827,083, 312 Amendment filed Dec. 10, 2002", 2 pgs.

"U.S. Appl. No. 09/827,083, Notice of Allowance mailed Sep. 10, 2002", 6 pgs.

"U.S. Appl. No. 09/827,083, Preliminary Amendment mailed Apr. 5, 2001", 5 pgs.

"U.S. Appl. No. 10/041,776, Non final office action mailed Dec. 31, 2002", 14 pgs.

"U.S. Appl. No. 10/041,776, Notice of allowance mailed Jul. 15, 2003", 14 pgs.

"U.S. Appl. No. 10/041,776, Response filed Apr. 30, 2003 to Non final office action mailed Dec. 31, 2002", 11 pgs.

"U.S. Appl. No. 10/263,379, Advisory Action mailed Mar. 1, 2006", 7 pgs.

"U.S. Appl. No. 10/263,379, Advisory Action mailed Apr. 11, 2006", 5 pgs.

"U.S. Appl. No. 10/263,379, Final Office Action mailed Nov. 1, 2006", 6 pgs.

"U.S. Appl. No. 10/263,379, Final Office Action mailed Nov. 9, 2005", 15 pgs.

"U.S. Appl. No. 10/263,379, Final Office Action mailed Nov. 23, 2004", 43 pgs.

"U.S. Appl. No. 10/263,379, Non-Final Office Action mailed Apr. 25, 2005", 13 pgs.

"U.S. Appl. No. 10/263,379, Non-Final Office Action mailed Jun. 14, 2006", 7 pgs.

"U.S. Appl. No. 10/263,379, Non-Final Office Action mailed Jun. 17, 2004", 35 pgs.

"U.S. Appl. No. 10/263,379, Notice of Allowance mailed Dec. 12, 2006", 4 pgs.

"U.S. Appl. No. 10/263,379, Response filed Feb. 8, 2006 to Final Office Action mailed Nov. 9, 2005", 19 pgs.

"U.S. Appl. No. 10/263,379, Response filed Feb. 23, 2005 to Final Office Action mailed Nov. 23, 2004", 20 pgs.

"U.S. Appl. No. 10/263,379, Response filed Apr. 4, 2006 to Final Office Action mailed Nov. 9, 2005 and Advisory Action mailed Mar. 1, 2006", 19 pgs.

"U.S. Appl. No. 10/263,379, Response filed Apr. 23, 2004 to Restriction Requirement mailed Mar. 24, 2004", 2 pgs.

"U.S. Appl. No. 10/263,379, Response filed May 2, 2006 to Final Office Action mailed Nov. 9, 2005 and Advisory Action mailed Apr. 11, 2006", 15 pgs.

"U.S. Appl. No. 10/263,379, Response filed Sep. 11, 2006 to Non Final Office Action mailed Jun. 14, 2006", 13 pgs.

"U.S. Appl. No. 10/263,379, Response filed Sep. 26, 2005 to Non Final Office Action mailed Apr. 25, 2005", 19 pgs.

"U.S. Appl. No. 10/263,379, Response filed Oct. 18, 2004 to Non Final Office Action mailed Jun. 17, 2004", 25 pgs.

"U.S. Appl. No. 10/263,379, Response filed Nov. 21, 2006 to Final Office Action mailed Nov. 1, 2006", 13 pgs.

"U.S. Appl. No. 10/263,379, Restriction Requirement mailed Mar. 24, 2004", 4 pgs.

"U.S. Appl. No. 10/379,154, 312 Amendment filed Apr. 4, 2007", 3 pgs.

"U.S. Appl. No. 10/379,154, Final Office Action mailed Feb. 17, 2004", 4 pgs.

"U.S. Appl. No. 10/379,154, Final Office Action mailed Mar. 30, 2006", 5 pgs.

"U.S. Appl. No. 10/379,154, Non-Final Office Action mailed Jun. 17, 2004", 4 pgs.

"U.S. Appl. No. 10/379,154, Non-Final Office Action mailed Aug. 1, 2005", 5 pgs.

"U.S. Appl. No. 10/379,154, Non-Final Office Action mailed Aug. 8, 2003", 4 pgs.

"U.S. Appl. No. 10/379,154, Non-Final Office Action mailed Dec. 15, 2004", 5 pgs.

"U.S. Appl. No. 10/379,154, Notice of Allowance mailed Jan. 4, 2007", 5 pgs.

"U.S. Appl. No. 10/379,154, Response filed May 16, 2005 to Non-Final Office Action mailed Dec. 15, 2004", 7 pgs.

"U.S. Appl. No. 10/379,154, Response filed May 17, 2004 to Final Office Action mailed Feb. 17, 2004", 6 pgs.

"U.S. Appl. No. 10/379,154, Response filed May 31, 2006 to Final Office Action mailed Mar. 30, 2006", 7 pgs.

"U.S. Appl. No. 10/379,154, Response filed Sep. 17, 2004 to Non-Final Office Action Jun. 17, 2004", 6 pgs.

"U.S. Appl. No. 10/379,154, Response filed Nov. 6, 2003 to Non-Final Office Action mailed Aug. 8, 2003", 8 pgs.

"U.S. Appl. No. 10/379,154, Response filed Dec. 1, 2005 to Non-Final Office Action mailed Aug. 1, 2005", 7 pgs.

"U.S. Appl. No. 10/412,726, Examiner Interview Summary mailed Mar. 21, 2007", 3 pgs.

"U.S. Appl. No. 10/412,726, Examiner Interview Summary mailed Apr. 23, 2007", 4 pgs.

"U.S. Appl. No. 10/412,726, Examiner Interview Summary mailed Apr. 26, 2007", 4 pgs.

"U.S. Appl. No. 10/412,726, Examiner Interview Summary mailed Jul. 11, 2006", 5 pgs.

"U.S. Appl. No. 10/412,726, Final Office Action mailed Jul. 19, 2007", 10 pgs.

"U.S. Appl. No. 10/412,726, Final Office Action mailed Jul. 23, 2008", 15 pgs.

"U.S. Appl. No. 10/412,726, Final Office Action mailed Oct. 8, 2004", 7 pgs.

"U.S. Appl. No. 10/412,726, Final Office Action mailed Dec. 5, 2005", 13 pgs.

"U.S. Appl. No. 10/412,726, Non Final Office Action mailed Mar. 16, 2005", 15 pgs.

"U.S. Appl. No. 10/412,726, Non Final Office Action mailed Apr. 7, 2004", 8 pgs.

"U.S. Appl. No. 10/412,726, Non Final Office Action mailed Oct. 30, 2006", 12 pgs.

"U.S. Appl. No. 10/412,726, Non-Final Office Action mailed Feb. 22, 2008", 10 pgs.

"U.S. Appl. No. 10/412,726, Non-Final Office Action mailed Apr. 16, 2010", 5 pgs.

"U.S. Appl. No. 10/412,726, Notice of Allowance mailed Mar. 12, 2009", 6 pgs.

"U.S. Appl. No. 10/412,726, Response filed Jan. 22, 2009 to Final Office Action mailed Jul. 23, 2008", 23 pgs.

"U.S. Appl. No. 10/412,726, Response filed Feb. 8, 2005 to Final Office Action mailed Oct. 8, 2004", 22 pgs.

"U.S. Appl. No. 10/412,726, Response filed Apr. 10, 2008 to Non-Final Office Action mailed Feb. 22, 2008", 30 pgs.

"U.S. Appl. No. 10/412,726, Response filed Apr. 27, 2007 to Non Final Office Action mailed Oct. 30, 2006", 23 pgs.

"U.S. Appl. No. 10/412,726, Response filed May 5, 2006 to Final office action mailed Dec. 5, 2005", 23 pgs.

"U.S. Appl. No. 10/412,726, Response filed Jul. 9, 2004 to Non Final Office Action mailed Jul. 9, 2004", 20 pgs.

"U.S. Appl. No. 10/412,726, Response filed Sep. 16, 2005 to Non Final Office Action mailed Mar. 16, 2005", 25 pgs.

"U.S. Appl. No. 10/412,726, Response filed Oct. 31, 2007 to Final Office Action mailed Jul. 19, 2007", 28 pgs.

"U.S. Appl. No. 11/002,008, Final office action mailed Apr. 2, 2007", 25 pgs.

"U.S. Appl. No. 11/002,008, Non Final office action mailed Jul. 13, 2006", 11 pgs.

"U.S. Appl. No. 11/002,008, Response filed Dec. 18, 2008 to Non Final office action mailed Jul. 13, 2006", 31 pgs.

"U.S. Appl. No. 11/002,008, Notice of Allowance mailed Dec. 12, 2007", 8 pgs.

"U.S. Appl. No. 11/002,008, Response filed Sep. 17, 2007 to Final Office Action mailed Apr. 2, 2007.", 26 pgs.

"U.S. Appl. No. 11/121,169, Non-Final Office Action Mailed Aug. 21, 2007", 8 pgs.

"U.S. Appl. No. 11/121,169, Notice of Allowance mailed Feb. 29, 2008", 6 pgs.

"U.S. Appl. No. 11/121,169, Response to Non-Final Office Action filed Dec. 20, 2007", 16 pgs.

"U.S. Appl. No. 11/196,529, Final Office Action mailed Dec. 2, 2008", 10 pgs.

"U.S. Appl. No. 11/196,529, Non-Final Office Action mailed Jun. 23, 2008", 11 pgs.

"U.S. Appl. No. 11/196,529, Notice of Allowance mailed Feb. 24, 2009", 8 pgs.

"U.S. Appl. No. 11/196,529, Preliminary Amendment filed Nov. 7, 2005", 20 pgs.

"U.S. Appl. No. 11/196,529, Response filed Dec. 19, 2008 to Final Office Action mailed Dec. 2, 2008", 19 pgs.

"U.S. Appl. No. 11/196,529, Response filed Aug. 7, 2008 to Non Final Office Action mailed Jun. 23, 2008", 21 pgs.

"U.S. Appl. No. 11/196,798, Non-Final Office Action mailed Mar. 31, 2008", 30 pgs.

"U.S. Appl. No. 11/196,798, Non-Final Office Action mailed Sep. 17, 2008", 6 pgs.

"U.S. Appl. No. 11/196,798, Notice of Allowance mailed Feb. 24, 2009", 5 pgs.

"U.S. Appl. No. 11/196,798, Response filed Feb. 8, 2008 to Restriction Requirement mailed Jan. 9, 2008", 18 pgs.

"U.S. Appl. No. 11/196,798, Response filed May 21, 2008 to Non Final Office Action mailed Apr. 21, 2008", 18 pgs.

"U.S. Appl. No. 11/196,798, Response filed Dec. 17, 2008 to Non-Final Office Action mailed Sep. 17, 2008", 17 pgs.

"U.S. Appl. No. 11/196,798, Restriction Requirement mailed Jan. 9, 2008", 6 pgs.

"U.S. Appl. No. 11/196,802, Notice of Allowance mailed Mar. 28, 2008", 33 pgs.

"U.S. Appl. No. 11/196,802, Preliminary Amendment filed Nov. 10, 2005", 16 pgs.

"U.S. Appl. No. 11/196,802, Response filed Feb. 8, 2008 to Restriction Requirement mailed Jan. 9, 2008", 16 pgs.

"U.S. Appl. No. 11/196,802, Restriction Requirement mailed Jan. 9, 2008", 6 pgs.

"U.S. Appl. No. 11/222,664, Non final office action mailed Mar. 16, 2007", 10 pgs.

"U.S. Appl. No. 11/222,664, Non final office action mailed Jul. 14, 2006", 28 pgs.

"U.S. Appl. No. 11/222,664, Preliminary Amendment mailed Jun. 17, 2006", 4 pgs.

"U.S. Appl. No. 11/222,664, Response filed Sep. 17, 2007 to Non-Final Office Action mailed Mar. 16, 2007.", 25 pgs.

"U.S. Appl. No. 11/222,664, Response filed Dec. 14, 2006 to Non final office action mailed Jul. 14, 2006", 28 pgs.

"U.S. Appl. No. 11/222,664, Notice of Allowance Mailed Dec. 12, 2007", 11 pgs.

"U.S. Appl. No. 11/497,280, Non-Final Office Action mailed Jun. 3, 2009", 14 pgs.

"U.S. Appl. No. 11/672,868, Examiner Interview Summary mailed Nov. 5, 2009", 2 pgs.

"U.S. Appl. No. 11/672,868, Non-Final Office Action mailed Apr. 13, 2009", 21 pgs.
"U.S. Appl. No. 11/672,868, Preliminary Amendment mailed Feb. 12, 2008", 15 pgs.
"U.S. Appl. No. 11/673,360, Final Office Action mailed Dec. 17, 2009", 27 pgs.
"U.S. Appl. No. 11/673,360, Non-Final Office Action mailed Apr. 22, 2009", 33 pgs.
"U.S. Appl. No. 11/673,360, Response filed Jun. 17, 2010 to Final Office Action mailed Dec. 17, 2009", 25 pgs.
"U.S. Appl. No. 11/673,360, Response filed Sep. 21, 2009 to Non Final Office Action mailed Apr. 22, 2009", 27 pgs.
"U.S. Appl. No. 11/691,374, Final Office Action mailed Jun. 17, 2009", 14 pgs.
"U.S. Appl. No. 11/691,374, Non Final Office Action mailed Sep. 29, 2009", 6 pgs.
"U.S. Appl. No. 11/691,374, Non-Final Office Action mailed Jan. 12, 2009", 40 pgs.
"U.S. Appl. No. 11/691,374, Notice of Allowance mailed Feb. 1, 2010", 7 pgs.
"U.S. Appl. No. 11/691,374, Preliminary Amendment filed Mar. 26, 2007", 3 pgs.
"U.S. Appl. No. 11/691,374, Preliminary Amendment filed Jun. 12, 2007", 21 pgs.
"U.S. Appl. No. 11/691,374, Received Jun. 17, 2010", 73 pgs.
"U.S. Appl. No. 11/691,374, Response filed Apr. 13, 2009 to Non Final Office Action mailed Jan. 12, 2009", 23 pgs.
"U.S. Appl. No. 11/691,374, Response filed Aug. 17, 2009 to Final Office Action mailed Jun. 17, 2009", 14 pgs.
"U.S. Appl. No. 11/691,374, Response filed Dec. 3, 2009 to Non Final Office Action mailed Sep. 29, 2009", 16 pgs.
"U.S. Appl. No. 11/739,680, Non-Final Office Action mailed Mar. 31, 2009", 20 pgs.
"U.S. Appl. No. 11/739,680, Preliminary Amendment filed Apr. 24, 2007", 3 pgs.
"U.S. Appl. No. 11/739,680, Supplemental Preliminary Amendment filed Jul. 18, 2007", 6 pgs.
"U.S. Appl. No. 12/487,235 Final Office Action mailed Sep. 20, 2010", 15 pgs.
"U.S. Appl. No. 12/487,235, Non-Final Office Action mailed Dec. 28, 2009", 7 pgs.
"U.S. Appl. No. 12/487,235, Response filed Jun. 28, 2010 to Non Final Office Action mailed Dec. 28, 2009", 12 pgs.
"U.S. Appl. No. 12/487,265, Non-Final Office Action mailed Dec. 18, 2009", 5 pgs.
"U.S. Appl. No. 12/487,265, Notice of Allowance mailed Apr. 6, 2010", 4 pgs.
"U.S. Appl. No. 12/487,265, Notice of Allowance mailed Sep. 7, 2010", 6 pgs.
"U.S. Appl. No. 12/487,265, Response filed Jan. 21, 2010 to Non Final Office Action mailed Dec. 18, 2009", 7 pgs.
"U.S. Appl. No. 12/630,231, Non Final Office Action mailed Jun. 28, 2010", 14 pgs.
"Australian Application Serial No. 2002362443, Examiner's First Report mailed May 29, 2007", 4 pgs.
"Australian Application Serial No. 2002362443, Response filed May 1, 2008 to Examiner's First Report mailed May 29, 2007", 46 pgs.
"Australian Application Serial No. 2005201255, Examiner's First Report mailed Apr. 13, 2007", 2 pgs.
"Australian Application Serial No. 2005201255, Response filed Feb. 7, 2008 to Examiner's Report dated Oct. 31, 2007", 6 pgs.
"Australian Application Serial No. 2005201255, Response filed Oct. 2, 2007 to Examiner's Report mailed Apr. 13, 2007", 8 pgs.
"Australian Application Serial No. 21082/99, Examiner's First Report dated Jun. 29, 2001", 3 pgs.
"Australian Application Serial No. 27454/00, Examiner's Report mailed Feb. 20, 2003", 1 pgs.
"Australian Application Serial No. 27454/00, Response filed Oct. 19, 2004 to Examiner's Report mailed Feb. 20, 2003", 14 pgs.
"Canadian Application Serial No. 2,361,614, Notice of Allowance mailed Mar. 26, 2008", 1 pg.
"Canadian Application Serial No. 2,361,614, Office Action mailed Jul. 20, 2007", 2 pgs.
"Canadian Application Serial No. 2,361,614, Response filed Nov. 7, 2007 to Office Action mailed Jul. 20, 2007", 9 pgs.
"Canadian Application Serial No. 2,375,374, Office Action Mailed Jan. 14, 2009", 11 pgs.
"Canadian Application Serial No. 2,375,374, Response filed Mar. 16, 2009 to Office Action Mailed Jan. 14, 2009", 7 pgs.
"Canadian Application Serial No. 2,460,911, Office Action mailed Apr. 16, 2010", 2 pgs.
"Canadian Application Serial No. 2,460,911, Office Action mailed Jun. 12, 2009", 7 pgs.
"Canadian Application Serial No. 2,460,911, Response filed Dec. 14, 2009 to Non Final Office Action mailed Jun. 12, 2009", 35 pgs.
"Canadian Application Serial No. 2375374, Notice of Allowance mailed Jul. 23, 2009", 1 pg.
"Chemical Abstracts Registry No. 152918-18-8", (Feb. 10, 1994), 1 pg.
"Chemical Abstracts Registry No. 250386-15-3", (Dec. 9, 1999), 1 pg.
"Chemical Abstracts Registry No. 287179-78-6", (Aug. 24, 2000), 1 pg.
"Chemical Abstracts Registry No. 313348-27-5", (Jan. 10, 2001), 1 pg.
"European Application Serial No. 00905833.0, Communication mailed Nov. 13, 2002", 3 pgs.
"European Application Serial No. 00905833.0, Response filed May 14, 2003 to Communication mailed Nov. 13, 2002", 12 pgs.
"European Application Serial No. 00941335.2-2110, Communication mailed Aug. 26, 2002", 4 pgs.
"European Application Serial No. 00941335.2-2110, Response filed Dec. 20, 2002 to Communication mailed Aug. 26, 2002", 10 pgs.
"European Application Serial No. 02800432.3, Communication mailed Jan. 13, 2005", 3 pgs.
"European Application Serial No. 02800432.3, Communication mailed Aug. 30, 2005", 2 pgs.
"European Application Serial No. 02800432.3, Communication mailed Sep. 20, 2004", 6 pgs.
"European Application Serial No. 02800432.3, Communication mailed Oct. 16, 2006", 5 pgs.
"European Application Serial No. 02800432.3, Office Action mailed Apr. 22, 2010", 3 Pgs.
"European Application Serial No. 02800432.3, Office Action Response Filed Jun. 23, 2010", 2 pgs.
"European Application Serial No. 02800432.3, Response filed Feb. 21, 2007 to Communication mailed Oct. 16, 2006", 19 pgs.
"European Application Serial No. 02800432.3, Response filed Nov. 1, 2005 to Communication mailed Aug. 30, 2005", 19 pgs.
"European Application Serial No. 03728372.8, Office Action mailed Apr. 11, 2005", 4 pgs.
"European Application Serial No. 03728372.8, Office Action mailed Nov. 24, 2005", 3 pgs.
"European Application Serial No. 03728372.8, Response filed Feb. 22, 2006 to Office Action mailed Nov. 24, 2005", 10 pgs.
"European Application Serial No. 03728372.8, Response filed Oct. 21, 2005 to Office Action mailed Apr. 11, 2005", 14 pgs.
"European Application Serial No. 05756108.6, Office Action mailed Aug. 6, 2010", 9 pgs.
"European Application U.S. Appl. No. 05803845.6, Communication mailed 07-26-07", 3 pgs.
"European Application Serial No. 05803845.6, Response filed Dec. 17, 2007 to Communication mailed Jul. 26, 2007", 28 pgs.
"European Application Serial No. 99901368.3, Communication dated Aug. 16, 2000", 2 pgs.
"International Application Serial No. PCT/US00/02324, International Preliminary Examination Report completed Apr. 5, 2001", 14 pgs.
"International Application Serial No. PCT/US00/02324, International Search Report mailed Oct. 20, 2000", 8 pgs.
"International Application Serial No. PCT/US00/02324, International Search Report mailed Oct. 20, 2000", 8 pgs.
"International Application Serial No. PCT/US00/02324, Response filed Mar. 1, 2001 to Written Opinion mailed Dec. 1, 2000", 13 pgs.
"International Application Serial No. PCT/US00/02324, Written Opinion mailed Dec. 1, 2000", 6 pgs.

"International Application Serial No. PCT/US00/02324, Written Opinion mailed Dec. 1, 2000", 6 pgs.

"International Application Serial No. PCT/US00/14548, International Search Report mailed Feb. 1, 2001", 4 pgs.

"International Application Serial No. PCT/US00/14548, Response filed May 20, 2001 to Written Opinion mailed Feb. 27, 2001", 13 pgs.

"International Application Serial No. PCT/US00/14548, Response filed Jul. 23, 2001 to Written Opinion mailed Jun. 25, 2001", 2 pgs.

"International Application Serial No. PCT/US00/14548, Written Opinion mailed Feb. 27, 2001", 7 pgs.

"International Application Serial No. PCT/US00/14548, Written Opinion mailed Jun. 25, 2001", 4 pgs.

"International Application Serial No. PCT/US00/16029, Amendment and Response filed Jun. 26, 2001 to Written Opinion mailed Apr. 26, 2001", 12 pgs.

"International Application Serial No. PCT/US00/16029, International Preliminary Examination Report completed Jul. 24, 2001", 14 pgs.

"International Application Serial No. PCT/US00/16029, International Search Report mailed Feb. 8, 2001", 6 pgs.

"International Application Serial No. PCT/US00/16029, Written Opinion mailed Apr. 26, 2001", 6 pgs.

"International Application Serial No. PCT/US02/31383, International Search Report mailed May 2, 2002", 8 pgs.

"International Application Serial No. PCT/US05/15241, International Search Report mailed Aug. 19, 2005", 3 pgs.

"International Application Serial No. PCT/US07/61919, International Search Report mailed Nov. 7, 2007", 3 pgs.

"International Application Serial No. PCT/US07/61919, International Search Report mailed Nov. 7, 2007", 3 pgs.

"International Application Serial No. PCT/US07/61919, Written Opinion mailed Nov. 7, 2007", 8 pgs.

"International Application Serial No. PCT/US07/61919, Written Opinion mailed Nov. 7, 2007", 8 pgs.

"International Application Serial No. PCT/US2005/015241, International Preliminary Examination Report mailed Nov. 16, 2006", 6 pgs.

"International Application Serial No. PCT/US2005/015241, International Search Report and Written Opinion mailed Sep. 14, 2005", 10 pgs.

"International Application Serial No. PCT/US2005/027474, International Preliminary Examination Report mailed Feb. 15, 2007", 10 pgs.

"International Application Serial No. PCT/US2005/027474, International Search Report and Written Opinion mailed Jan. 25, 2006", 16 pgs.

"International Application Serial No. PCT/US2005/027474, Search Report for mailed Jan. 25, 2006", 5 pgs.

"International Application Serial No. PCT/US2005/027475, International Preliminary Examination Report mailed Feb. 15, 2007", 7 pgs.

"International Application Serial No. PCT/US2005/027475, International Search Report mailed Jan. 23, 2006", 6 pgs.

"International Application Serial No. PCT/US2005/027475, Written Opinion mailed Jan. 23, 2006", 8 pgs.

"International Application Serial No. PCT/US2005/027479, International Preliminary Examination Report mailed Feb. 15, 2007", 12 pgs.

"International Application Serial No. PCT/US2005/027479, International Search Report mailed Spe. 6, 2006", 6 pgs.

"International Application Serial No. PCT/US2005/027479, International Search Report mailed Sep. 6, 2006", 6 pgs.

"International Application Serial No. PCT/US2005/027479, Written Opinion mailed Sep. 6, 2006", 10 pgs.

"International Application Serial No. PCT/US2007/061867, International Preliminary Examination Report mailed Aug. 21, 2008", 8 pgs.

"International Application Serial No. PCT/US2007/061867, International Search Report mailed Nov. 26, 2007", 3 pgs.

"International Application Serial No. PCT/US2007/061867, Written Opinion mailed Nov. 26, 2007", 8 pgs.

"International Application Serial No. PCT/US2007/061919, International Preliminary Examination Report mailed Aug. 21, 2008", 8 pgs.

"International Application Serial No. PCT/US2008/004553, International Preliminary Examination Report mailed Oct. 22, 2009", 8 pgs.

"International Application Serial No. PCT/US2008/004553, International Search Report mailed Jul. 30, 2008", 2 pgs.

"International Application Serial No. PCT/US2008/004553, Written Opinion mailed Jul. 30, 2008", 7 pgs.

"International Application Serial No. PCT/US99/00366, International Preliminary Examination Report completed Mar. 20, 2000", 9 pgs.

"International Application Serial No. PCT/US99/00366, International Search Report mailed Mar. 20, 2000", 7 pgs.

"International Application Serial No. PCT/US99/00366, Remarks and Response filed Jan. 5, 2000 to Written Opinion mailed Oct. 29, 1999", 2 pgs.

"International Application Serial No. PCT/US99/00366, Written Opinion mailed Oct. 29, 1999", 8 pgs.

"Merriam-Webster's Collegiate Dictionary", Tenth Edition, (1998), 924 and 935.

"Taber's Cyclopedic Medical Dictionary, 19th Edition", Venes, et al. (eds.), F. A. Davis, Philadelphia, (2001), 960-961.

Abiru, T., et al., "Differential vasodilatory action of 2-octynyladenosine (YT-146), an adenosine A2 receptor agonist, in the isolated rat femoral artery and vein.", Eur J Pharmacol., 281(1), (Jul. 25, 1995), 9-15.

Abiru, T., et al., "Nucleosides and nucleotides. 107. 2-(cycloalkylalkynyl)adenosines: adenosine A2 receptor agonists with potent antihypertensive effects", Journal of Medicinal Chemistry, 35(12), (Jun. 12, 1992), 2253-2260.

Adah, S. A., "Synthesis of Complex Ethynyladenosines Using Organic Triflic Enolates in Palladium-Catalyzed Reactions: Potential Agonists for the Adenosine A2 Receptor", Tetrahedron, 53, (1997), 6747-6754.

Ali, H., et al., "Methylxanthines Block Antigen-induced Responses in RBL-2H3 Cells Independently of Adenosine Receptors or Cyclic AMP: Evidence for Inhibition of Antigen Binding to IgE", Journal of Pharmacology and Experimental Therapeutics, 258, (1991), 954-962.

Andersson, P., et al., "Anti-anaphylactic and anti-inflammatory effects of xanthines in the lung", Curr. Clin. Pract. Ser., (1985), 187-192.

Andrews, F. J., et al., "Effect of Nonsteroidal Anti-Inflammatory Drugs on LFA-1 and ICAM-1 Expression in Gastric Mucosa", American Journal of Physiology—Gastrointestinal and Liver Physiology, 266, (1994), G657-G664.

Appleyard, C. B., et al., "Tumor Necrosis Factor Mediation of NSAID-Induced Gastric Damage: Role of Leukocyte Adherence", American Journal of Physiology—Gastrointestinal and Liver Physiology, 33, (1996), G42-G48.

Auchampach, J. A., et al., "A3 adenosine receptor agonist IB-MECA reduces myocardial ischemia-reperfusion injury in dogs", Am J Physiol Heart Circ Physiol vol. 285, (2003), H607-H613.

Ballas, S. K, "Sickle Cell Anaemia: Progress in Pathogenesis and Treatment", Drugs vol. 62 No. (8), (2002), 1143-1172.

Baraldi, Pier G., et al., "Synthesis and Biological Activity of a New Series of N6-Arylcarbamoyl, 2-(Ar)alkynyl-N6-arylcarbamoyl, and N6-Carboxamido derivatives of adenosine-5'-N-ethyluronamide as A1 and A3 Adenosine receptor agonists", Journal of Medicinal Chemistry, 41(17), (Aug. 13, 1998), 3174-3185.

Barold, S. S., et al., "Significance of Transient Electrocardiographic Q Waves in Coronary Artery Diseasse", Cardiology Clinics, 5(3), (Aug. 1987), 367-380.

Beck, P. L., et al., "Mechanisms of NSAID-Induced Gastrointestinal Injury Defined Using Mutant Mice", Gastroenterology, 119(3), (2000), 699-705.

Beers, M. H, et al., "The Merck Manual of Diagnosis and Therapy", Merck Research Laboratories, (1999), 245-256.

Belcher, J. D., et al., "Transgenic Sickle Mice Have Vascular Inflammation", Blood, 101(10), (2003), 3953-3959.

Berkich, D. A., et al., "Evidence of Regulated Coupling of A1 Adenosine Receptors by Phosphorylation in Zucker Rats.", American Journal of Physiology, 268(4), (Apr. 1995), E693-E704.

Bhattacharya, S., et al., "Effects of Long-term Treatment With the Allosteric Enhancer, PD81,723, on Chinese Hamster Ovary Cells Expressing Recombitant Human A1 Adenosine Receptors", Molecular Pharmacology, 50(1), (Jul. 1996), 104-111.

Bhattacharya, S., et al., "The Allosteric Enhancer, PD 81,723, Stabilizes Human A1 Adenosine Receptor Coupling to G Proteins", Biochimica et Biophysica Acta, 1265 (1), (Feb. 1995), 15-21.

Bradford, M. M., "A Rapid and Sensitive Method for the Quantitation of Microgram Quantities of Protein Utilizing the Principle of Protein-Dye Binding", Analytical Biochemistry, 72, (1976), 248-254.

Bridges, A. J., et al., "N6-[2-(3,5-Dimethoxyphenyl)-2-(2-Methylphenyl)-Ethyl]Adenosine and Its Uronamide Derivatives. Novel Adenosine Agonists With Both High Affinity and High Selectivity for the Adenosine A2 Receptor", Journal of Medicinal Chemistry, 31(7), (Jul. 1988), 1282-1285.

Brito, G. A. C., et al., "Clostridium difficile Toxin A Induces Intestinal Epithelial Cell Apoptosis and Damage: Role of Gln and Ala-Gln in Toxin A Effects", Digestive Diseases and Sciences, 50(7), (2005), 1271-1278.

Brodie, D. A., et al., "A Study of the Factors Involved in the Production of Gastric Ulcers by the Restraint Technique", Gastroenterology, 38(3), (1960), 353-360.

Bruns, R. F., "Adenosine Receptors—Roles and Pharmacology", Biological Actions of Extracellular ATP, 603, Annals of The New York Academy of Sciences, (1990), 211-226.

Bruns, R. F., et al., "Characterization of the A2 Adenosine Receptor Labeled by [3H]NECA in Rat Striatal Membranes", Molecular Pharmacology, 29, (1986), 331-346.

Buchanan, G. R., et al., "Sickle Cell Disease", Hematology 2004, (2004), 35-47.

Buster, B., et al., "The Effect of Adenosine Receptor Agonists on Neutrophil Pleocytosis and Blood-Brain Barrier Pathophysiology in Experimental Bacterial Meningitis", Abstract of the Interscience Conference on Antimicrobial Agents and Chemotherapy, 37, Abstract No. B-72, (1997), 39.

Camaioni, E, et al., "Adenosine receptor agonists: synthesis and bilogical evaluation of the diastereoisomers of 2-(3-Hydroxy-3-phenyl-1-propyn-1-yl)NECA", Bioorganic & Medicinal Chemistry, 5(12), (Dec. 1997), 2267-75.

Cargnoni, et al., "Role of A2A Receptors in the Modulation of Myocardial Reperfusion damage", Journal of Cardiovascular Pharmacology vol. 33 No. (6), (1999), pp. 883-893.

Carruthers, A. M., et al., "Hypotensive Responses to the Putative Adenosine A3 Receptor Agonist N6-2-(4-Aminophenyl)-Ethyladenosine in the Rat", Drug Development Research, 30, (1993), 147-152.

Cassada, D C, et al., "Adenosine A2A agonist reduces paralysis after spinal cord ischemia: correlation with A2A receptor expression on motor neurons", Annals of Thoracic Surgery, 74(3), (Sep. 2002), 846-9; discussion 849-50.

Cassada, D C, et al., "Adenosine A2A analogue ATL-146e reduces systemic tumor necrosing factor-alpha and spinal cord capillary platelet-endothelial cell adhesion molecule-1 expression after spinal cord ischemia", Journal of Vascular Surgery, 35(5), (May 2002), 994-98.

Cassada, D C, et al., "Adenosine A2A analogue improves neurologic outcome after spinal cord trauma in the rabbit.", Journal of Trauma-Injury Infection & Critical Care, 53(2), (Aug. 2002), 225-9.

Cassada, D C, et al., "Adenosine Analogue Reduces Spinal Cord Reperfusion Injury in a Time-Dependent Fashion", Surgery, 130(2), (Aug. 2001), 230-35.

Cassada, D C, et al., "An adenosine A2A agonist, ATL-146e, reduces paralysis and apoptosis during rabbit spinal cord reperfusion.", Journal of Vascular Surgery, 34(3), (Sep. 2001), 482-88.

Cassada, D C, et al., "Systemic adenosine A2A agonist ameliorates ischemic reperfusion injury in the rabbit spinal cord", Annals of Thoracic Surgery, 72(4), (Oct. 2001), 1245-50.

Cavalcante, I. C, et al., "Effect of Novel A2A Adenosine Receptor Agonist ATL 313 on Clostridium difficile Toxin A-Induced Murine Ileal Enteritis", Infection and Immunity, vol. 74, No. 5, (May 2006), 2606-2612.

Cembrzynska-Nowak, M, et al., "Elevated Release of Tumor Necrosis Factor-alpha and Interferon-gamma by Bronchoalveolar Leukocytes From Patients With Bronchial Asthma.", American Review of Respiratory Disease, 147(2), (1993), 291-295.

Charache, S., et al., "Effect of Hydroxyurea on the Frequency of Painful Crisis in Sickle Cell Anemia", The New England Journal of Medicine, 332(20), (1995), 1317-1322.

Chies, J. A. B., et al., "Sickle Cell Disease: A Chronic Inflammatory Condition", Medical Hypotheses, 57(1), (2001), 46-50.

Chou, T. C., et al., "Quantitative analysis of dose-effect relationships: the combined effects of multiple drugs or enzyme inhibitors", Advances in Enzyme Regulation, 22, (1984), 27-55.

Chow, F., et al., "Macrophages in mouse type 2 diabetic nephropathy: correlation with diabetic state and progressive renal injury", Kidney Int., 65(1), XP002593910, ISSN: 0085-2538, (Jan. 2004), 116-28.

Cohen, S. B, et al., "Adenosine-2 alpha analogue augments the treatment in experimental infectious arthritis", Poster presented at the 48th Annual Meeting of the Orthopaedic Research Society, Dallas, USA, (Feb 10-13, 2002), Poster No: 0689.

Cothran, D. L., et al., "Ontogeny of Rat Myocardial A1 Adenosine Receptors", Biol Neonate, 68 (2), (1995), 111-118.

Cristalli, G, et al., "2-Alkynyl Derivatives of Adenosine-5'-N-ethyluronamide: Selective A2 Adenosine Receptor Agonists with Potent Inhibitory Activity on Platelet Aggregation", Journal of Medicinal Chemistry, 37(11), (1994), 1720-1726.

Cristalli, G, et al., "Platelet aggregation inhibitory activity of selective A2 Adenosine Receptor Agonists", Nucleosides & Nucleotides, vol. 14 No. 3-5, (1995), 449-453.

Cristalli, G., "2-Alkynyl Derivatives of Adenosine an Adenosine-5'-N-ethyluronamide as Selective Agonists at A2 Adenosine Receptors", Journal of Medicinal Chemistry, 35 (13), (1992), 2363-2368.

Cristalli, G., et al., "2-Aralkynyl and 2-Heteroalkynyl Derivatives of Adenosine-5'-N-ethyluronamide as Selective A2a Adenosine Receptor Agonists", J. Med. Chem., 38 (9), (1995), 1462-1472.

Cristalli, G., et al., "Characterization of Potent Ligands at Human Recombinant Adenosine Receptors", Drug Development Research, 45, Research Overview, (1998), 176-181.

Cronstein, B N., et al., "Neutrophil Adherence to Endothelium is Enhanced Via Adenosine A1 Receptors and Inhibited Via Adenosine A2 Receptors", The Journal of Immunology, 148 (7), (1992), 2201-2206.

Cronstein, B. N, et al., "Adenosine modulates the generation of superoxide anion by stimulated human neutrophils via interaction with a specific cell surface receptor.", Ann N Y Acad Sci., 451, (1985), 291-301.

Cronstein, B. N., "Adenosine, an Endogenous Anti-Inflammatory Agent", Journal of Applied Physiology, 76(1), (1994), 5-13.

Cronstein, B. N., "Adenosine; A Physiologic Modulator of Superoxide Anion Generated by Human Neutrophils. Adenosine Acts Via an A2 Receptor on Human Neutrophils", Journal of Immunology, 135(2), (1985), 1366-1371.

Cronstein, B. N., "Engagement of Adenosine Receptors Inhibits Hydrogen Peroxide (H2O2) Release by Activated Human Neutrophils", Clinical Immunology and Immunopathology, 42(1), (1987), 76-85.

Cronstein, B. N., "Methotrexate Inhibits Leukocyte Influx Into Inflammatory Sites Via The Adenosine (A2) Receptor", Clinical Research, 41(2), (1993), 244A.

Cronstein, B. N., et al., "Occupancy of Adenosine Receptors Raises Cyclic AMP Alone and in Synergy With Occupancy of Chemoattractant Receptors and Inhibits Membrane Depolarization", Biochemical Journal, 252 (3), (1988), 709-715.

Cronstein, B. N., "The Adenosine/Neutrophil Paradox Resolved: Human Neutrophils Possess Both A1 and A2 Receptors That Promote Chemotaxis and Inhibits 02 Generation, Respectively", Journal of Clinical Investigation, 85(4), (1990), 1150-1157.

Day, Y., et al., "A2A adenosine receptors on bone marrow-derived cells protect liver from ischemia-reperfusion injury", The Journal of Immunology, 174(8), (Apr. 15, 2005), 5040-6.

Day, Y. J., et al., "Renal Protection from Ischemia Mediated by A2A Adenosine Receptors on Bone Marrow-Derived Cells.", Journal of Clinical Investigation, 112(6), (2003), 883-891.

Day, Y.-J., et al., "Protection From Ischemic Liver Injury by Activation of A2A Adenosine Receptors During Reperfusion: Inhibition of Chemokine Induction", American Journal of Physiology Gastrointestinal and Liver Physiology, 286, (2004), G285-293.

De La Harpe, J., "Adenosine Regulates the Respiratory Burst of Cytokine—Triggered Human Neutrophils Adherent to Biological Surfaces", Journal of Immunology, 143(2), (1989), 596-602.

De Moraes, V. L., et al., "Effect of Cyclo-Oxygenase Inhibitors and Modulators of Cyclic AMP Formation on Lipopolysaccharide-Induced Neutrophil Infiltration in Mouse Lung", British Journal of Pharmacology, 117, (1996), 1792-1796.

De Sarro, G., et al., "Effects of adenosine Receptor Agonists and Antagonists on Audiogenic Seizure-sensible DBA / 2 mice", European Journal of Pharmacology, 371, (1999), 137-145.

De Zwart, M, et al., "5-N-Substituted Carboxamidoadenosines as Agonists for Adenosine Receptors", Journal of Medicinal Chemistry, 42(8), (Apr. 22, 1999), 1384-1392.

Dechatelet, L R., et al., "Mechanism of the Luminol-Dependent Chemiluminescence of Human Neutrophils", The Journal of Immunology, 129(4), (1982), 1589-1593.

Dinarello, C. A., "Interleukin-1 and Tumor Necrosis Factor: Effector Cytokines in Autoimmune Diseases", Seminars in Immunology, 4, (1992), 133-145.

Doyle, M. P., et al., "Nucleoside-induced Arteriolar Constriction: a Mast Cell-dependent Response.", American Journal of Physiology, 266(5), (May 1994), H2042-H2050.

Elzein, E., et al., "Design, Synthesis and Biological Evaluation of 2-(4-Substituted-N-Pyrazolyl)-Adenosine Derivatives As Novel Short Acting Adenosine A2A Receptor Agonists", Drug Development Research, 50(1), Abstracts From Purines 2000: Biochemical, Pharmacological, and Clinical Perspectives: Abstract No. 061, (May 2000), 64.

Entman, M. L., et al., "Inflammation in the course of early myocardial ischemia", FASEB Journal, vol. 5, (1991), 2529-2537.

Fabry, M. E., et al., "High Expression of Human beta S—and alpha-globins in Transgenic Mice: Hemoglobin Composition and Hematological Consequences", Proc. Natl. Acad. Sci. USA, 89, (1992), 12150-12154.

Fabry, M. E., et al., "High Expression of Human beta s—and alpha-globins in Transgenic Mice: Erythrocyte Abnormalities, Organ Damage, and the Effect of Hypoxia", Proc. Natl. Acad. Sci. USA, 89, (1992), 12155-12159.

Fang, G. D, et al., "ATL 146e (ATL), a Selective A[2A] Adenosine Receptor Agonist, Combined with Ceftriaxone, Markedly Improves Survival in a Mouse Model of E. coli 026:B6 Sepsis", Meeting Abstract B-1110, Presented at the 41st Interscience Conference on Antimicrobial Agents and Chemotherapy, Chicago, USA, (Dec. 16-19, 2001), 5 pgs.

Fang, G. D., et al., "DWH146e (DWH), A New Selective Adenosine A2a Receptor Agonist, Improves Survival in E. coli 026:B6 Lipopolysaccharide (LPS)-Induced Experimental Murine Endotoxemia", Journal of Investigative Medicine, Abstract No. 797, (2000), 148A.

Fenster, M. S., et al., "Activation of adenosine A2 alpha receptors inhibits mast cell degranulation and mast cell-dependent vasoconstriction", Microcirculation, 7(2), (Apr. 2000), 129-135.

Feoktistov, I., et al., "Adenosine A2B receptors", The American Society for Pharmacological and Experimental Therapeutics, 49(4), (1997), 381-402.

Feoktistov, I., et al., "Role of Adenosine in Asthma", Drug Development Research, 39, (1996), 333-336.

Ferrante, A., "Optimal Conditions for Simultaneous Purification of Mononuclear and Polymorphonuclear Leucocytes From Human Blood by the Hypaque-Ficoll Method", Journal of Immunological Methods, 36(2), (1980), 109-117.

Figler, R. A., et al., "Reconstitution of Bovine A1 Adenosine Receptors and G Proteins in Phospholipid Vesicles: .Beta..Gamma.-Subunit Composition Influences Guanine Nucleotide Exchange and Agonist Binding", Biochemistry, 36(51), (1997), 6288-16299.

Figler, R. A., et al., "Reconstitution of Recombinant Bovine A1 Adenosine Receptors in Sf9 Cell Membranes with Recombinant G Proteins of Defined Composition.", Molecular Pharmcology, 50(6), (Dec. 1996), 1587-1595.

Firestein, G. S, "Adenosine Regulating Agents: A Novel Approach to Inflammation and Inflammatory Arthritis", Clinical Research, 41(2), (Abstract Only), (1993), 170A.

Fiser, S M, et al., "Adenosine A2A receptor activation decreases reperfusion injury associated with high-flow reperfusion.", Journal of Thoracic & Cardiovascular Surgery, 124(5), (Nov. 2002), 973-8.

Fozard, J. R., et al., "Adenosine A3 Receptors Mediate Hypotension in the Angiotensin II-supported Circulation of the Pithed Rat", British Journal of Pharmacology, 109(1), (1993), 3-5.

Francis, J. E., "Highly Selective Adenosine A2 Receptor Agonists in a Series of N-Alkylated 2-Aminoadenosines", Journal of Medicinal Chemistry, 34 (8), (1991), 2570-2579.

Frangogiannis, N G, et al., "The Role of the Neutrophil in Myocardial Ischemia and Reperfusion", Myocardial Iscehmia: Mechanisms, Reperfusion, Protection, M. Karmazyn, Editor, Birkhauser Verlag Basel, (1996), 236-284.

Frenette, P. S., "Sickle Cell Vasoocclusion: Heterotypic, Multicellular Aggregations Driven by Leukocyte Adhesion", Microcirculation, 11, (2004), 167-177.

Gao, Z, et al., "Purification of A1 Adenosine Receptor-G-protein Complexes: Effects of Receptor Down-regulation and Phosphorylation on Coupling", Biochemical Journal, 338 (Pt3), (1999), 729-736.

Gao, Z., et al., "A2B Adenosine and P2Y2 Receptors Stimulate Mitogen-activated Protein Kinase in Human Embryonic Kidney-293 Cells. Cross-talk Between Cyclic AMP and Protein Kinase c Pathways", Journal of Biological Chemistry, 274(9), (Feb. 26, 1999), 5972-5980.

Gilchrist, A., et al., "Antagonists of the Receptor-G Protein Interface Block Gi-coupled Signal Transduction", Journal of Biological Chemistry, 273(24), (Jun. 12, 1998), 14912-14919.

Girardi, N, et al., "Inflammatory Aneurysm of the Ascending Aorta and Aortic Arch", Ann. Thor. Surg., 64, (1997), 251-253.

Glover, D K, et al., "Pharmacological stress myocardial perfusion imaging with the potent and selective A(2A) adenosine receptor agonists ATL193 and ATL146e administered by either intravenous infusion or bolus injection", Circulation, 104(10), (Sep. 4, 2001), 1181-1187.

Glover, D. K., et al., "Bolus Injection of DWH-146E, A Novel Adenosine A2A Receptor Agonist for Use in Vasodilator Stress Imaging", Journal of Nuclear Cardiology, 7(4), Abstract No. 44.20, (Sep. 23, 2000), 1 pg.

Glover, D. K., et al., "Characterization of a New, Highly Selective Adenosine A2A Receptor Agonist with Potential Use in Pharmacologic Stress Perfusion Imaging", Circulation, 100, Abstract, (1999), 1 pg.

Glover, D. K., et al., "Pharmacological stress thallium scintigraphy with 2-cyclohexylmethylidenehydrazinoadenosine (WRC-0470). A novel, short-acting adenosine A2A receptor agonist.", Circulation, 94(7), (Oct. 1, 1996), 1726-1732.

Glover, D. K., et al., "Vasodilator Stress Imaging Using New Adenosine A2A Receptor Agonists Administered by Bolus Injection", J. Am. Coll. Cardiol., 35, (Abstract), (2000), 1 pg.

Griswold, D. E., et al., "Effect of Selective Phosphodiesterase Type IV Inhibitor, Rolipram, on Fluid and Cellular Phases of Inflammatory Response", Inflammation, 17(3), (1993), 333-344.

Hall, J., et al., "Abnormal Hypothalamic-Pituitary-Adrenal Axis Function in Rheumatoid Arthritis", Arthritis & Rheumatism, 37(8), (1994), 1132-1137.

Hamaguchi, M., et al., "Mechanisms and Roles of Neutrophil Infiltration in Stress-Induced Gastric Injury in Rats", Digestive Diseases and Sciences, 46(12), (2001), 2708-2715.

Hamajima, E., et al., "Effects of FK506, An Immunosuppressive Agent, on Genesis of Water-Immersion Stress-Induced Gastric Lesions in Rats", Digestive Diseases and Sciences, 39(4), (1994), 713-720.

Hanlon, W. A., "rTNF alpha Facilitate Human Polymorphonuclear Leukocyte Adherence to Fibrinogen Matrices With Mobilization of Specific and Tertiary But Not Azurophilic Granule Markers", Journal of Leukocyte Biology, 50 (1), (1991), 43-48.

Harada, N., et al., "Adenosine and Selective A2a Receptor Agonists Reduce Ischemia/Reperfusion Injury of Rat Liver Mainly by Inhibiting Leukocyte Activation", The Journal of Pharmacology and Experimental Therapeutics, 294(3), (2000), 1034-1042.

Harada, N., et al., "Adenosine reduces ischemia/reperfusion injury of rat liver by inhibiting leukocyte activation: Involvement of adenosine A2a receptor", Jpn. J. Pharmacol., 79(Suppl), Abstract No. 0-214, (1999), 89P.

Hartung, H. P., "Immune-Mediated Demyelination", Annals of Neurology, 33 (6), (Jun. 1993), 563-567.

Hasko, G., et al., "Adenosine Inhibits IL-12 and TNF-alpha Production via Adenosine A2a Receptor-Dependent and Independent Mechanisms", The FASEB Journal, 14, (2000), 2065-2074.

Hatley, M. E., et al., "Increased Production of 12/15 Lipoxygenase Eicosanoids Accelerates Monocyte/Endothelial Interactions in Diabetic db/db Mice", The Journal of Biological Chemistry, 278(28), (2003), 25369-25375.

Hebbel, R. P., "Special Issue of Microcirculation: Examination of the Vascular Pathobiology of Sickle Cell Anemia", Microcirculation, 11, (2004), 99-100.

Hebbel, R. P., et al., "The Endothelial Biology of Sickle Cell Disease: Inflammation and a Chronic Vasculopathy", Microcirculation, 11, (2004), 129-151.

Heller, L. J., et al., "Effect of Adenosine on Histamine Release and Atrioventricular Conduction During Guinea Pig Cardiac Anaphylaxis", Circulation Research, 62(6), (Jun. 1988), 1147-1158.

Hogan, C. J., et al., "Inhibiting the inflammatory response in joint sepsis", Arthroscopy, 17(3), (Mar. 2001), 311-315.

Holmes, D, R, et al., "Restenosis after percutaneous transluminal coronary angioplasty (PTCA): a report from the PTCA Registry of the National Heart, Lung, and Blood Institute.", Am J Cardiol., 53(12), (Jun. 15, 1984), 77C-81C.

Homma, H, et al., "Nucleosides and nucleotides. 112. 2-(1-Hexyn-1-yl)adenosine-5'- uronamides: a new entry of selective A2 adenosine receptor agonists with potent antihypertensive activity.", Journal of Medicinal Chemistry, 35(15), (Jul. 1992), 2881-90.

Hussain, T., et al., "125I-APE Binding to Adenosine Receptors in Coronary Artery: Photoaffinity Labeling With 125I-azidoAPE", The Journal of Pharmacology and Experimental Therapeutics, 276(1), (Jan. 1996), 284-288.

Hutchison, A. J., et al., "2-(Arylalkylamino)adenosin-5'-uronamides: a new class of highly selective adenosine A2 receptor ligands.", J Med Chem., 33(7), (Jul. 1990), 1919-24.

Hutchison, A. J., et al., "CGS 21680C, an A2 selective adenosine receptor agonist with preferential hypotensive activity.", J Pharmacol Exp Ther., 251(1), (Oct. 1989), 47-55.

Iannone, M. A., "Effects of Adenosine on Human Neutrophil Function and Cyclic AMP Content", In: Topics and Perspectives in Adenosine Research, Eds. E. Gerlach et al., Springer-Verlag, Berlin, Germany, (1986), 286-298.

Imagawa, D. K., et al., "The role of tumor necrosis factor in allograft rejection. III. Evidence that anti-TNF antibody therapy prolongs allograft survival in rats with acute rejection.", Transplantation, 51(1), (Jan. 1991), 57-62.

Ishiwata, K., et al., "Further Characterization of a CNS Adenosine A2a Receptor Ligand [11C]KF18446 with in vitro Autoradiography and in vivo Tissue Uptake", Annals of Nuclear Medicine, 14 (2), Abstract Only, Obtained from Chemicals Abstracts, 133, Abstract No. 346544, HCAPlus Accession No. 480897 (2000), (2000), 81-89.

Ito, B. R., et al., "Role of Cardiac Mast Cells in Complement C5a-induced Myocardial Ischemia", American Journal of Physiology—Heart and Circulatory Physiology, 264(5), (May 1993), H1346-H1354.

Jarvis, M. F., "[3H]CGS 21680, A Selective A2 Adenosine Receptor Agonist Directly Labels A2 Receptors in Rat Brain.", Journal of Pharmacology and Experimental Therapeutics, 251(3), (Dec. 1989), 888-893.

Jolly, S. R., "Effects of Lodoxamide on Ischemic Reperfused Myocardium", Journal of Cardiovascular Pharmacology, 4(3), (1982), 441-448.

Jordan, J. E., et al., "Adenosine A2 Receptor Activation Attenuates Reperfusion Injury by Inhibiting Neutrophil Accumulation, Superoxide Generation and Coronary Endothelial Adherence", The Journal of Pharmacology and Experimental Therapeutics, 280(1), (1997), 301-309.

Kahky, M. P., et al., "Portal Infusion of Tumor Necrosis Factor Increases Mortality in Rats", Journal of Surgical Research, 49(2), (1990), 138-145.

Kaminuma, O., et al., "Effect of T-440, a Novel Type IV Phosphodiesterase Inhibitor, on Allergen-Induced Immediate and Late Asthmatic Reaction and Leukocyte Infiltration into the Airways of Guinea Pigs", International Archives of Allergy & Immunology, 112(4), (1997), 406-411.

Kanko, et al., "Protective Effects of Clopidogrel on Oxidant Damage in a Rat Model of Acute Ischemia", Tohoku J. Exp. Med., 205, (2005), 133-139.

Kaul, D. K., et al., "Anti-Inflammatory Therapy Ameliorates Leukocyte Adhesion and Microvascular Flow Abnormalities in Transgenic Sickle Mice", American Journal of Physiology—Heart and Circulatory Physiology, 287, (2004), H293-H301.

Kaul, D. K., et al., "Hypoxia/Reoxygenation Causes Inflammatory Response in Transgenic Sickle Mice but Not in Normal Mice", The Journal of Clinical Investigation, 106(3), (2000), 411-420.

Keller, A. M., "Acute Reoxygeneration Injury in the Isolated Rat Heart: Role of Resident Cardiac Mast Cells", Circulation Research, 63(6), (Dec. 1988), 1044-1052.

Kennedy, A. P., et al., "Covalent modification of transmembrane span III of the A1 adenosine receptor with an antagonist photoaffinity probe.", Mol Pharmacol., 50(4), (Oct. 1996), 789-98.

Klotz, Karl-Norbert, et al., "2-Substituted N-ethylcarboxamidoadenosine derivatives as high-affinity agonists at human A3 adenosine receptors", Naunyn-Schmiedebergs Archives of Pharmacology, 360(2), (Aug. 1999), 103-108.

Knapp, C. M., et al., "The Type IV Phosphodiester Inhibitors, Ro 20-1724 and Rolipram,Block the Initiation of Cocaine Self Administration", Pharmocology, Biochemistry and Behavior,62(1), (Jan. 1999), 151-158.

Kokura, S., et al., "T-Lymphocyte-Derived Tumor Necrosis Factor Exacerbates Anoxia-Reoxygenation-Induced Neutrophil-Endothelial Cell Adhesion", Circulation Research, 86, (2000), 205-213.

Kollias-Baker, C., et al., "Allosteric Enhancer PD 81,723 Acts by Novel Mechanism to Potentiate Cardiac Actions of Adenosine", Circulation Research, 75(6), (Dec. 1994), 961-971.

Koshiba, M, et al., "Patterns of A2A Extracellular Adenosine Receptor Expression in Different Functional Subsets of Human Peripheral T Cells. Flow Cytometry Studies With Anti-A2A Receptors Monoclonal Antibodies.", Molecular Pharmacology, 55(3), (Mar. 1999), 614-624.

Koshiba, M., "Patterns of A2A Extracellular Adenosine Receptor Expression in Different Functional Subsets of Human Peripheral T Cells", The FASEB Journal, Abstract No. 703.38, (1999), A944.

Krawisz, J. E., et al., "Quantitative Assay for Acute Intestinal Inflammation Based on Myeloperoxidase Activity", Gastroenterology, 87(6), (1984), 1344-1350.

Lappas, C. M, et al., "A2A adenosine receptor induction inhibits IFN-gamma production in murine CD4+ T cells", Journal of Immunology, 174(2), (Jan. 15, 2005), 1073-1080.

Lard, L. R., "Neutrophil Activation in Sickle Cell Disease", Journal of Leukocyte Biology, 66, (1999), 411-415.

Leclerc, G., et al., "Percutaneous Arterial Gene Transfer in a Rabbit Model", Journal of Clinical Investigation, 90(3), (1992), 936-944.

Legrand-Poels, S., et al., "Activation of Human Immunodeficiency Virus Type 1 by Oxidative Stress", AIDS Research and Human Retroviruses, 6(12), (1990), 1389-1397.

Lette, J., et al., "Safety of Dipyridamole Testing in 73,806 Patients: The Multicenter Dipyridamole Safety Study", Journal of Nuclear Cardiology, 2(1), (1995), 3-17.

Linden, J, "Cloned Adenosine A3 Receptors: Pharmacological Properties, Species Differences and Receptor Functions.", Trends in Pharmacological Sciences, 15(8), (Aug. 1994), 298-306.

Linden, J, et al., "The structure and function of A1 and A2B adenosine receptors.", Life Sci., 62(17-18), (1998), 1519-24.

Linden, J., et al., "[125I]Aminobenzyladenosine, a New Radioligand with Improved Specific Binding to Adenosine Receptors in Heart", Circulation Research, 56(2), (Feb. 1985), 279-284.

Linden, J., "Calculating the Dissociation Constant of an Unlabeled Compound from the Concentration Required to Displace Radiolabel Binding by 50%", Journal of Cyclic Nucleotide Research, 8(3), (1982), 163-172.

Linden, J., et al., "Chapter 2—Adenosine Receptors", In: Handbook of Receptors and Channels—G Protein Coupled Receptors, Peroutka, S. J., Editor, CRC Press, Boca Raton, FL, (1994), 29-44.

Linden, J., "Chapter 2—Recombinant Techniques as Applied to the Study of A1 Adenosine Receptors", In: Adenosine and Adenine Nucleotides: From Molecular Biology to Integrative Physiology, Belardinelli, L., Editor, Kluwer Academic Publishers, Boston, (1995), 15-19.

Linden, J., "Chapter 5—Allosteric Enhancement of Adenosine Receptors", In: Purinergic Approaches in Experimental Therapeutics, Edited by K.A. Jacobson et al., and Published by Wiley-Liss, Inc., (1997), 85-97.

Linden, J., "Molecular Approach to Adenosine Receptors: Receptor-Mediated Mechanisms of Tissue Protection", Annual Review of Pharmacology and Toxicology, 41, (2001), 775-787.

Linden, J., et al., "Molecular Cloning and Functional Expression of a Sheep A3 Adenosine Receptor with Widespread Tissue Distribution", Molecular Pharmacology, 44(3), (1993), 524-532.

Link, A. A., et al., "Ligand-Activation of the Adenosine A2a Receptors Inhibits IL-12 Production by Human Monocytes", The Journal of Immunology, 164, (2000), 436-442.

Lum, A. F. H., et al., "Inflammatory Potential of Neutrophils Detected in Sickle Cell Disease", American Journal of Hematology, 76, (2004), 126-133.

Luthin, D. R., et al., "Adenosine Receptors", Biomembranes, 2B, (1996), 321-347.

Luthin, D. R., "Characterization of Two Affinity States of Adenosine A2a Receptors With a New Radioligand, 2-[2-(4-amino-3-[125I]iodophenyl) Ethylamino]Adenosine.", Molecular Pharmacology, 47(2), (Feb. 1995), 307-313.

Luthin, D. R, et al., "Comparison of A4 and A2a binding sites in striatum and COS cells transfected with adenosine A2a receptors.", J Pharmacol Exp Ther., 272(2), (Feb. 1995), 511-8.

Luthin, D. R, et al., "Photoaffinity labeling with 2(−)[2-(4-azido-3(−)[125I]- iodophenyl)ethylamino]adenosine and autoradiography with 2(−)[2-(4-amino-3(−)[125I]iodophenyl)ethylamino]adenosine of A2a adenosine receptors in rat brain.", J Neurochem., 65(5), (Nov. 1995), 2072-9.

Mager, P. P., "Neural network approaches applied to selective A2a adenosine receptor agonists", Med. Chem. Res., 8(6), (1998), 277-290.

Mahan, L. C., et al., "Cloning and Expression of an A1 Adenosine Receptor from Rat Brain", Molecular Pharmacology, 40(1), (Jul. 1991), 1-7.

Mannel, D. N., et al., "Tumor Necrosis Factor: A Cytokine Involved in Toxic Effects of Endotoxin", Reviews of Infectious Diseases, 9(Suppl. 5), (1987), S602-S606.

March, Jerry, "", Advanced Organic Chemistry: Reactions, Mechanisms, and Structure, Fourth Edition, (1992), p. 400.

Martin, P. L., et al., "Characterization of 8-(N-Methylisopropyl)Amino-N6-(5'-Endohydroxy-endonorbornyl)-9-methyladenine (WRC-0571), a Highly Potent and Selective, Non-xanthine Antagonist of A1 Adenosine Receptors.", The Journal of Pharmacology and Experimental Therapeutics, 276(2), (Feb. 1996), 490-499.

Martin, P. L., et al., "Pharmacology of 2-cyclohexylmethylidenehydrazinoadenosine (WRC-0470), a Novel, Short-acting Adenosine A2A Receptor Agonist That Produces Selective Coronary Vasodilation.", Drug Development Research, 40(4), (1997), 313-324.

Matherne, G. P., et al., "Transgenic A1 adenosine receptor overexpression increases myocardial resistance to ischemia.", Proc Natl Acad Sci U S A., 94(12), (Jun. 10, 1997), 6541-6.

Matsuyama, T., "Cytokines and HIV Infection: is AIDS a Tumor Necrosis Factor Disease?", AIDS, 5(12), (1991), 1405-1417.

McGarrity, S. T., "Inhibition of Neutrophil Superoxide Anion Generation by Platelet Products: Role of Adenine Nucleotides", Journal of Leukocyte Biology, 44(5), (1988), 411-421.

McGarrity, S. T., "Regulation of Human Neutrophil Function by Adenine Nucleotides", Journal of Immunology, 142(6), (1989), 1986-1994.

McLaughlin, D. P., et al., "Hemodynamic and Metabolic Correlates of Dipyridamole-induced Myocardial Thallium-201 Perfusion Abnormalities in Multivessel Coronary Artery Disease.", American Journal of Cardiology, 73(16), (Jun. 1994), 1159-1164.

McPherson, J A, "Adenosine A(2A) receptor stimulation reduces inflammation and neointimal growth in a murine carotid ligation model", Arteriosclerosis, Thrombosis & Vascular Biology, 21(5), (May 2001), 791-6.

McPherson, J. A., et al., "Effect of Prolonged Adenosine A2A Receptor Activation on Neointimal Formation in the Injured Mouse Carotid Artery", The FASEB Journal, Abstract No. 299.2, (1999), p. A367.

McPherson, J. A., et al., "Prolonged Adenosine A2a Receptor Stimulation Reduces Inflammation and Neointima Formation in a Murine Carotoid Ligation Model", Supplement to Circulation, 100 (18), Abstract No. 3652, (Nov. 2, 1999), 1 pg.

Miyamoto, F, et al., "Retinal Cytokine Response in Mouse Alkali-Burned Eye", Opthalmic Research, 30, (1997), 168-171.

Mizumura, T., et al., "PD 81,723, an Allosteric Enhancer of the A1 Adenosine Receptor, Lowers the Threshold for Ischemic Preconditioning in Dogs.", Circulation Research, 79(3), (Sep. 1996), 415-423.

Molnar-Kimber, K., et al., "Modulation of TNF alpha and IL-1 beta from endotoxin-stimulated monocytes by selective PDE isozyme inhibitors.", Agents Actions., 39, (1993), C77-9.

Moore, C. C., et al., "A2A Adenosine Receptor Agonists Modify Inflammatory Responses in an E. coli Peritonitis Murine Septic Shock Model", Proceedings of the 43rd Annual Meeting of the Infectious Disease Society of America, Abstract No. 52, (Oct. 6-9, 2005), p. 43.

Morabito, L., et al., "Methotrexate and Sulfasalazine Promote Adenosine Release by a Mechanism that Requires Ecto-5'-Nucleotidase-mediated Conversion of Adenine Nucleotides", Journal of Clinical Investigation, 101(2), (1998), 295-300.

Mumby, S. M., et al., "G-protein alpha-subunit expression, myristoylation, and membrane association in COS cells", Proc. Natl. Acad. Sci. USA. 87(2), (Jan. 1990), 728-732.

Murphree, L. J., et al., "Human A2a Adenosine Receptors: High-Affinity Agonist Binding to Receptor-G Protein Complexes Containing GBeta4", Molecular Pharmacology, 61(2), (2002), 455-462.

Nabel, E. G, et al., "Site-specific gene expression in vivo by direct gene transfer into the arterial wall.", Science, 249(4974), (Sep. 14, 1990), 1285-8.

Nagel, R. L., et al., "Review—The Panoply of Animal Models for Sickle Cell Anaemia", British Journal of Haematology, 112, (2001), 19-25.

Needleman, J. P., et al., "Breathing Patterns During Vaso-occlusive Crisis of Sickle Cell Disease", Chest, 122(1), (2002), 43-46.

Newman, K. D., "Adenovirus-mediated Gene Transfer into Normal Rabbit Arteries Results in Prolonged Vascular Cell Activation, Inflammation and Neointimal Hyperplasia", Journal of Clinical Investigation, 96(6), (1995), 2955-2965.

Nielson, C. P., "Effects of Adenosine on Polymorphonuclear Leucocyte Function, Cyclic 3': 5'-adenosine Monophosphate, and Intracellular Calcium", British Journal of Pharmacology, 97(3), (1989), 882-888.

Niiya, K., "2-(N'-Alkylidenehydrazino)Adenosines: Potent and Selective Coronary Vasodilators", Journal of Medicinal Chemistry, 35(24), (1992), 4557-4561.

Nolte, D., et al., "Reduction of Postischemic Leukocyte-Endothelium Interaction by Adenosine Via A2 Receptor", Naunyn-Schmiedeberg's Archives of Pharmacology, 346(2), (1992), 234-237.

Odashima, M., et al., "Attenuation of Gastric Mucosal Inflammation Induced by Aspirin Through the Activation of A2a Adenosine Receptor in Rats", World Journal of Gastroenterology, 12(4), (2006), 6 pgs.

Odashima, M., et al., "Selective Adenosine A2 Receptor Agonist, ATL-146e, Attenuates Stress-Induced Gastric Lesions in Rats", Journal of Gastroenterology and Hepatology, 20(2), (2005), 275-280.

Okusa, M D, et al., "A(2A) Adenosine Receptor-Mediated Inhibition of Renal Injury and Neutrophil Adhesion", American Journal of Physiology—Renal Fluid & Electrolyte Physiology, 279(5), (2000), F809-F818.

Okusa, M D, et al., "Enhanced Protection from Renal Ischemia: Reperfusion Injury With A2A-Adenosine Receptor Activation and PDE 4 Inhibition", Kidney International, 59(6), (2001), 2114-2125.

Okusa, M. D, "A(2A) adenosine receptor: a novel therapeutic target in renal disease", Am J Physiol Renal Physiol., 282(1), XP002593908; ISSN : 0002-9513, (Jan. 2002), F10-8.

Okusa, M. D., et al., "Selective A2A adenosine receptor activation reduces ischemia-reperfusion injury in rat kidney", Am. J. Physiol., 277(3, Pt 2), (1999), F404-F412.

Okusa, Mark D, "Attenuation of renal inflammation by adenosine 2A receptor (A2A-AR) activation in ischemia-reperfusion injury (I/R) Regulation adhesion molecule and cytokine expression", 33RD Annual Meeting of the American Society of Nephrology vol. 11, No . Program and A, XP008124542; ISSN : 1046-6673, (Sep. 1, 2000), 132A.

Olah, M. E., et al., "Adenosine Receptor Subtypes: Characterization and Therapeutic Regulation", Annual Review of Pharmacology and Toxicology, 35, (1995), 581-606.

Olsson, R. A., et al., "N6 Substituted N-Alkyladenosine-5'-Uronamides: Bifunctional Ligands Having Recognition Groups for A1 and A2 Adenosine Receptors", Journal of Medicinal Chemistry, 29(9), (1986), 1683-1689.

O'Regan, M. H., et al., "Adenosine Receptor Agonists Inhibit the Release of y-Aminobutyric Acid (GABA) From the Ischemic Rat Cerebral Cortex", Brain Research, 582(1), (1992), 22-26.

Orringer, E. P., et al., "Purified Poloxamer 188 for Treatment of Acute Vaso-occlusive Crisis of Sickle Cell Disease", JAMA, 286(17), (2001), 2099-2106.

Osuka, M. D, et al., "Enhanced protection from renal ischemia-reperfusion [correction of ischemia:reperfusion] injury with A(2A)-adenosine receptor activation and PDE 4 inhibition", Kidney Int., 59(6), (Jun. 2001), 2114-25.

Pathare, A., et al., "Hemoglobinopathy—Cytokines in Sickle Cell Disease", Hematology, 8(5), (2003), 329-337.

Peart, J, et al., "Adenosine-mediated cardioprotection in ischemic-reperfused mouse heart.", Journal of Cardiovascular Pharmacology, 39(1), (Jan. 2002), 117-129.

Peet, N. P., et al., "Conformationally Restrained, Chiral (Phenylisopropyl)Amino-Substituted Pyrazolo[3,4-d]Pyrimidines and Purines With Selectivity for Adenosine A1 and A2 Receptors", Journal of Medicinal Chemistry, 35 (17), (1992), 3263-3269.

Peirce, S M, "Selective A(2A) adenosine receptor activation reduces skin pressure ulcer formation and inflammation", American Journal of Physiology—Heart & Circulatory Physiology, 281(1), (Jul. 2001), H67-H74.

Peirce, S. M., et al., "Attenuation of I/R Injury in Skin Using A Selective A2A Adenosine Receptor Agonist", FASEB Journal, 14(4), Abstract No. 333.1, (Mar. 15, 2000), p. A466.

Pennell, R L, et al., "Inflammatory abdominal aortic aneurysms: A thirty-year review", Journal of Vascular Surgery, 2, (1985), 859-869.

Pfister, J. R., et al., "Synthesis and Biological Evaluation of the Enantiomers of the Potent and Selective A1-adenosine Antagonist 1,3-dipropyl-8[2-(5,6-epoxynorbonyl)]-xanthine", Journal of Medicinal Chemistry, 40 (12), (1997), 1773-1778.

Pflueger, A. C, et al., "Adenosine-Induced Renal Vasoconstriction in Diabetes Mellitus Rats: Role of Nitric Oxide", Am. J. Physiol. Renal Physiol., 276, (1999), F340-F346.

Platt, O. S., et al., "Pain in Sickle Cell Disease—Rates and Risk Factors", The New England Journal of Medicine, 325(1), (1991), 11-15.

Platt, O. S., "Sickle Cell Anemia as an Inflammatory Disease", The Journal of Clinical Investigation, 106(3), (2000), 337-338.

Pulle, V., et al., "Design, Synthesis And Pharmacological Evaluation of 2(1-Alkyl-Pyrazol-4-YL) Adenosine Derivatives As Short Acting Adenosine A2A Receptor Agonists", Drug Development Research, 50(1), Abstracts From Purines 2000: Biochemical, Pharmacological and Clinical Perspectives: Abstract No. 062, (May 2000), 64.

Raitt, M. H., et al., "Abnormal Q Waves are Common Early in AMI and Do Not Predict Decreased Myocardial Salvage With Thrombolytic Therapy", Special Issue Journal of American College of Cardiology, Abstract No. 895-77, (Feb. 1994), p. 195A.

Ranhosky, A., et al., "The safety of intravenous dipyridamole thallium myocardial perfusion imaging. Intravenous Dipyridamole Thallium Imaging Study Group.", Circulation, 81(4), (Apr. 1990), 1205-9.

Rashad, S., et al., "Effect of Non-Steroidal Anti-Inflammatory Drugs on the Course of Osteoarthritis", The Lancet, 2(8662), (Sep. 2, 1989), 519-522.

Rieger, J. M, et al., "Design, Synthesis, and Evaluation of Novel A2A Adenosine Receptor Agonists", J. Med. Chem., 44, (2001), 531-539.

Riou, L M, et al., "Influence of propranolol, enalaprilat, verapamil, and caffeine on adenosine A(2A)-receptor-mediated coronary vasodilation", Journal of the American College of Cardiology, 40(9), (Nov. 6, 2002), 1687-1694.

Roberts, P. A., et al., "Inhibition by Adenosine of Reactive Oxygen Metabolite Production by Human Polymorphonuclear Leucocytes", Biochemical Journal, 227(2), (1985), 669-674.

Robeva, A. S., et al., "Double Tagging Recombitant A1- and A2A-Adenosine Receptors With Hexahistidine and the FLAG Epitope. Development of an Efficient Generic Protein Purification Procedure.", Biochemical Pharmacology, 51(4), (Feb. 1996), 545-555.

Robeva, A. S., et al., "Molecular Characterization of Recombinant Human Adenosine Receptors", Drug Development Research, 39, (1996), 243-252.

Rosin, D. L., et al., "Immunohistochemical Localization of Adenosine A2A Receptors in the Rat Central Nervous System", The Journal of comparative Neurology, 401, (1998), 163-186.

Ross, R., "The Pathogenesis of Atherosclerosis: A Perspective for the 1990s", Nature, 362, (Apr. 29, 1993), 801-809.

Ross, S D, et al., "Selective Adenosine-A2A Activation Reduces Lung Reperfusion Injury Following Transplantation", Journal of Heart & Lung Transplantation, 18(10), (1999), 994-1002.

Ross, S. D, et al., "Selective Adenosine-A2A Activation Reduces Lung Reperfusion Injury Following Transplantation", Journal of Heart and lung transplantation, 18 (1), Abstract Only, Proceedings of the Nineteenth Annual Meeting and Scientific Sessions of the International Society for Heart and Lung Transplantation, San Francisco, CA, (Jan. 1999), p. 72.

Rothe, G. A., et al., "Flow Cytometric Measurement of the Respiratory Burst Activity of Phagocytes Using Dihydrorhodamine 123", Journal of Immunological Methods, 138(1), (1991), 133-135.

Santucci, L., et al., "Pentoxifylline Prevents Indomethacin Induced Acute Gastric Mucosal Damage in Rats: Role of Tumour Necrosis Factor Alpha", Gut, 35, (1994), 909-915.

Saunthararajah, Y., et al., "Effects of 5-aza-2'-deoxycytidine on Fetal Hemoglobin Levels, Red Cell Adhesion, and Hematopoietic Differentiation in Patients With Sickle Cell Disease", Blood, 102(12), (2003), 3865-3870.

Sawmiller, D. R., et al., "Effects of Xanthine Amine Congener on Hypoxic Resistence and Venous and Epicardial Adenosine Concentrations.", Cardiovascular Research, 28(5), (May 1994), 604-609.

Schiffmann, S. N., et al., "Distribution of adenosine A2 receptor mRNA in the human brain.", Neurosci Lett., 130(2), (Sep. 16, 1991), 177-81.

Schlack, W., et al., "Adenosine A2-Receptor Activation at Reperfusion reduces Infarct Size and Improves Myocardial Wall Function in Dog Heart", Journal of Cardiovascular Pharmacology, 22, (1993), 89-96.

Schrier, D. J., et al., "The Effects of Adenosine Agonists on Human Neutrophil Function", Journal of Immunology, 137(10), (1986), 3284-3289.

Seekamp, A., "Ischemia—Reperfusion Injury", Agents and Actions Supplements, 41, (1993), 137-152.

Shapiro, B. S., "The Management of Pain in Sickle Cell Disease", Pediatric Clinics of North America, 36(4), (1989), 1029-1041.

Sharief, M. K, et al., "Elevated serum levels of tumor necrosis factor-alpha in Guillain-Barré syndrome.", Ann Neurol., 33(6), (Jun. 1993), 591-6.

Sharma, H S, et al., "Role of cytokines in myocardial ischemia and reperfusion", Med. of Inflamm., 6, (1987), 175-183.

Shay, H., et al., "A Simple Method for the Uniform Production of Gastric Ulceration in the Rat", Gastroenterology, 5(1), (1945), 43-61.

Sheardown, M. J, "Unexpected Neuroprotection Observed with the Adenosine A2A Receptor Agonist CGS 21860", Drug Development Research, 39, (1996), 108-114.

Shepherd, R. K, et al., "Adenosine-induced vasoconstriction in vivo. Role of the mast cell and A3 adenosine receptor.", Circ Res., 78(4), (Apr. 1996), 627-34.

Shi, W., et al., "Endothelial Responses to Oxidized Lipoproteins Determine Genetic Susceptibility to Atherosclerosis in Mice", Circulation, 102, (2000), 75-81.

Silverman, R., "Chapter 2, Drug Discovery, Design and Development", The Organic Chemistry of Drug Design and Drug Action, San Diego : Academic Press, (1992), 4-47.

Sipka, S., et al., "Adenosine Induced Delay of Expression of AIDS Virus, HIV, in H9T Cells", Acta. Biochimica et Biophysica Hungarica, 23(1), (1988), 75-82.

Siragy, H. M, et al., "Sodium intake markedly alters renal interstitial fluid adenosine.", Hypertension, 27(3 Pt 1), (Mar. 1996), 404-7.

Smits, P., et al., "Cardiovascular effects of two xanthines and the relation to adenosine antagonism.", Clin Pharmacol Ther., 45(6), (Jun. 1989), 593-9.

Solovey, A., "Circulating Activated Endothelial Cells in Sickle Cell Anemia", The New England Journal of Medicine, 337(22), (1997), 1584-1590.

Solovey, A., et al., "Tissue Factor Expression by Endothelial Cells in Sickle Cell Anemia", Journal of Clinical Investigation, 101(9), (1998), 1899-1904.

Steinberg, M. H., et al., "Effect of Hydroxyurea on Mortality and Morbidity in Adult Sickle Cell Anemia", JAMA, 289(13), Correction, published in JAMA, 290(6)(2003) at p. 756, (2003), 1645-1651.

Stuart, M. J., et al., "Sickle-Cell Disease", The Lancet, 364, (2004), 1343-1360.

Sullivan, G W., et al., "Interactions of Human Neutrophils with Leukotoxic *Streptococci*", Infection and Immunity, 30 (1), (1980), pp. 272-280.

Sullivan, G. W., "A2A Adenosine Receptor Activation Improves Survival in Mouse Models of Endotoxemia and Sepsis", Journal of Infectious Diseases, 189(10), (May 15, 2004), 1897-1904.

Sullivan, G. W., "Adenosine (ADO) Modulates Endotoxin and TNF-Induced PMN Activation", Clinical Research, 41(2), (1993), 172A.

Sullivan, G. W., et al., "Adenosine and Related Compounds Counteract Tumor Necrosis Factor ~a Inhibition of Neutrophil Migration: Implication of a Novel Cyclic AMP-Independent Action on the Cell Surface", The Journal of Immunology, 145(5), (1990), 1537-1544.

Sullivan, G. W., et al., "Neutrophil A2A Adenosine Receptor Inhibits Inflammation in a Rat Model of Meningitis: Synergy with the Type IV Phosphodiesterase Inhibitor, Rolipram", The Journal of Infectious Diseases, 180, No. 5, (1999), pp. 1550-1560.

Sullivan, G. W., et al., "Role of A2A Adenosine Receptors in Inflammation", Drug Development Research, 45 (3/4), (1998), 103-112.

Sullivan, G. W., et al., "The role of inflammation in vascular diseases", Journal of Leukocyte Bilogy, 67, (May 2000), 591-602.

Sullivan, G. W., et al., "The Specific Type IV Phosphodiesterase Inhibitor Rolipram Combined with Adenosine Reduces Tumor Necrosis Factor-a-Primed Neutrophil Oxidative Activity", International Journal of Immunopharmacology, 17(10), (1995), 793-803.

Sullivan, G. W., "Two Methylxanthines, Pentoxifylline (PTX) and Caffeine (CAF) Have Divergent Effects on Tumor Necrosis Factor (TNF)-Primed Human Neutrophil (PMN) Activation", Clinical Research, 41(2), (1993), p. 172A.

Sullivan, Gail W., et al., "Cyclic AMP-Dependent Inhibition of Human Neutrophil Oxidative Activity by Substitued 2-Propynylcyclohexyl Adenosine A2A Receptor Agonists", British Journal of Pharmacology, 132(5), (2001), 1017-1026.

Takahashi, T., et al., "Increased spontaneous adherence of neutrophils from type 2 diabetic patients with overt proteinuria: possible role of the progression of diabetic nephropathy.", Diabetes Care, 23(3), XP002593909; ISSN: 0149-5992, (Mar. 2000), 417-8.

Takeuchi, K., et al., "Oxygen Free Radicals and Lipid Peroxidation in the Pathogenesis of Gastric Mucosal Lesions Induced by Indomethacin in Rats", Digestion, 49(3), (1991), 175-184.

Takiguchi, Y., et al., "Early administration of YT-146, an adenosine A2 receptor agonist, inhibits neointimal thickening after rat femoral artery endothelium injury.", Eur J Pharmacol., 281(2), (Aug. 4, 1995), 205-7.

Terrosu, P., et al., "Angiographic Correlate of Post-Reperfusion Abnormal Q Waves", Japanese Heart Journal, 29(2), (Mar. 1988), 179-187.

Tomer, A., "Platelet Activation as a Marker for in vivo Prothrombotic Activity: Detection by Flow Cytometry", Journal of Biological Regulators and Homeostatic Agents, 18, (2004), 172-177.

Topol, E. J., et al., "Randomised Trial of Coronary Intervention With Antibody Against Platelet IIb/IIIa integrin for Reduction of Clinical Restenosis: Results at Six Months", The Lancet, 343(8902), (1994), 881-886.

Tracey, K. J., "Cachectin/Tumor Necrosis Factor Induces Cachexia, Anemia, and Inflammation", Journal of Experimental Medicine, 167, (Mar. 1988), 1211-1227.

Tucker, A. L, et al., "A1 adenosine receptors. Two amino acids are responsible for species differences in ligand recognition", Journal of Biological Chemistry, 269(45), (Nov. 11, 1994), 27900-27906.

Turhan, A., et al., "Primary Role for Adherent Leukocytes in Sickle Cell Vascular Occlusion: A New Paradigm", Proc. Natl. Acad. Sci. USA, 99(5), (2002), 3047-3051.

Ueeda, M., et al., "2-Alkoxyadenosines: Potent and Selective Agonists at the Coronary Artery A2 Adenosine Receptor", Journal of Medicinal Chemistry, 34(4), (1991), 1334-1339.

Ukena, D., et al., "Species differences in structure-activity relationships of adenosine agonists and xanthine antagonists at brain A1 adenosine receptors.", FEBS Lett., 209(1), (Dec. 1, 1986), 122-8.

Underwood, D. C, et al., "Inhibition of antigen-induced bronchoconstriction and eosinophil infiltration in the guinea pig by the cyclic AMP-specific phosphodiesterase inhibitor, rolipram.", J Pharmacol Exp Ther., 266(1), (Jul. 1993), 306-13.

Van Calker, D., et al., "Carbamazepine distinguishes between adenosine receptors that mediate different second messenger responses", Eur J Pharmacol., 206(4), (Apr. 25, 1991), 285-90.

Van Calker, Dietrich, et al., "Adenosine regulates via two different types of receptors, the accumulation of cyclic AMP in cultured brain cells", J Neurochem., 33(5), (Nov. 1979), 999-1005.

Vittori, S, et al., "2-alkenyl and 2-alkyl derivatives of adenosine and adenosine-5'-N-ethyluronamide: different affinity and selectivity of E- and Z-diastereomers at A2A adenosine receptors.", Journal of Medicinal Chemistry, 39(21), (Oct. 1996), 4211-7.

Volpini, R., et al., "Synthesis of Di- and Tri-Substituted Adenosine Derivatives and Their Affinities at Human Adenosine Receptor Subtypes", Nucleosides & Nucleotides, 18 (11,12), (1999), 2511-2520.

Wagner, M. C., "Sickle Cell Adhesion Depends on Hemodynamics and Endothelial Activation", J. Lab. Clin. Med., 144, (2004), 260-267.

Walker, Blair A., et al., "Adenosine A2a Receptor Activation Delays Apoptosis in Human Neutrophils", The Journal of Immunology, 158, (1997), 2926-2931.

Walker, D I, et al., "Inflammatory Aneurysms of the Abdominal Aorta", Brit. J. Surg., 59, (1972), 609-614.

Wallace, J. L., et al., "Gastric Ulceration Induced by Nonsteroidal Anti-Inflammatory Drugs is a Neutrophil-Dependent Process", American Journal of Physiology Gastrointestinal and Liver Physiology, 259, (1990), G462-G467.

Wan, W., et al., "Binding of the adenosine A2 receptor ligand [3H]CGS 21680 to human and rat brain: evidence for multiple affinity sites.", J Neurochem., 55(5), (Nov. 1990), 1763-71.

Weiner, D. L., "Preliminary Assessment of Inhaled Nitric Oxide for Acute Vaso-occulsive Crisis in Pediatric Patients With Sickle Cell Disease", JAMA, 289(9), Correction, published in JAMA, 292(8), (2004) at p. 925, (2003), 1136-1142.

Wolff, A. A., et al., "Ventricular Arrhythmias Parallel Cardiac Histamine Efflux After Coronary Artery Occlusion in the Dog", Agents and Actions, 25 (3/4), (1988), 296-306.

Wood, K C., et al., "Endothelial Cell P-Selectin Mediates a Proinflammatory and Prothrombogenic Phenotype in Cerebral Venules of Sickle Cell Transgenic Mice", American Journal of Physiology—Heart and Circulatory Physiology, 286, (2004), H1608-H1614.

Wun, T., et al., "Platelet-Erythrocyte Adhesion in Sickle Cell Disease", Journal of Investigative Medicine, 47(3), (1999), 121-126.

Yale, S. H., et al., "Approach to the Vaso-Occlusive Crisis in Adults With Sickle Cell Disease", American Family Physician, 61(5), Correction, published in American Family Physician, 64(2) (2001), p. 220, (2000), 1349-1356, 1363-1364.

Yoneyama, F., et al., "Vasodepressor mechanisms of 2-(1-octynyl)-adenosine (YT-146), a selective adenosine A2 receptor agonist, involve the opening of glibenclamide-sensitive K+ channels.", Eur J Pharmacol., 213(2), (Mar. 24, 1992), 199-204.

Yoshida, N., et al., "Role of Neutrophil-Mediated Inflammation in Aspirin-Induced Gastric Mucosal Injury", Digestive Diseases and Sciences, 40(11), (1995), 2300-2304.

Yoshikawa, T., et al., "Augmentative Effects of Tumor Necrosis Factor-Alpha (Human, Natural Type) on Polymorphonuclear Leukocyte-Derived Superoxide Generation Induced by Various Stimulants", International Journal of Immunopharmacology, 14(8), (1992), 1391-1398.

Yoshikawa, T., et al., "Role of Active Oxygen, Lipid Peroxidation, and Antioxidants in the Pathogenesis of Gastric Mucosal Injury Induced by Indomethacin in Rats", Gut,34(6), (1992), 732-737.

Zablocki, J., et al., "Novel Short Acting Coronary Vasodilators That Are Functionally Selective for the A2A Receptor Based on 2-Heterocyclic Substituted Adenosine Derivatives", Drug Development Research, 50(1), Abstracts From Purines 2000: Biochemical, Pharmacological and Clinical Perspectives: Abstract No. 059, (May 2000), 63.

Zhang, X., et al., "Cellular Accumulation and Retention of the Technetium-99m-Labelled Hypoxia Markers BRU59-21 and Butylene Amine Oxime", Nuclear Medicine and Biology, 28, (2001), 949-957.

Zipursky, A., et al., "Oxygen Therapy in Sickle Cell Disease", The American Journal of Pediatric Hematology/Oncology, 14(3), (1992), 222-228.

"U.S. Appl. No. 10/412,726, Examiner Interview Summary mailed Nov. 30, 2010", 2 pgs.

"U.S. Appl. No. 11/497,280, Examiner Interview Summary mailed Dec. 16, 2009", 2 pgs.

"U.S. Appl. No. 11/673,360, Non Final Office Action mailed Nov. 26, 2010", 26 pgs.

"U.S. Appl. No. 12/487,235, Examiner Interview Summary Dec. 7, 2010", 3 pgs.

"U.S. Appl. No. 12/712,022, Non-Final Office Action mailed Nov. 9, 2010", 53 pgs.

"Australian Application Serial No. 2005267706, Examiner Report mailed on Sep. 16, 2010", 2 Pgs.

"Canadian Application Serial No. 2,460,911, Office Action Response Filed Oct. 14, 2010", 4 pgs.

"European Application Serial No. 05803845.6, Communication mailed Oct. 18, 2010", 4 pages.

"European Application Serial No. 10181920.9, Extended European Search Report mailed Nov. 30, 2010", 11 pgs.

"Japanese Application Serial No. 2000-596019, Office Action Response Filed Nov. 15, 2010", 23 pgs.

"Singapore Application Serial No. 200706337-3, Response to Written Opinion Filed: Dec. 13, 2010", 15 pgs.

"U.S. Appl. No. 12/712,022, Final Office Action mailed Aug. 24, 2011", 10 pgs.

"U.S. Appl. No. 12/712,022, Response filed Jun. 23, 2011 to Non Final Office Action mailed Mar. 23, 2011", 19 pgs.

"European Application Serial No. 05756108.6, Response filed Jul. 20, 2011 to Non Final Office Action dated Feb. 3, 2011", 22 pgs.

"European Application Serial No. 10181920.9, Office Action mailed Jul. 21, 2011", 4 pgs.

"European Divisional Application Serial No. 10181920.9, Response filed Jun. 29, 2011 to EP Search Report dated Nov. 30, 2011", 53 pgs.

"Japanese Application Serial No. 2001-504939, Final Office Action mailed Jul. 28, 2011", 6 pgs.

"Japanese Application Serial No. 2007-511486, Office Action Response filed Aug. 5, 2011 to Office Action mailed Feb. 23, 2011", 29 pgs.

"Japanese Application Serial No. 2007-524924, Office Action mailed Sep. 16, 2011", 1 pgs.

"New Zealand Application Serial No. 585697, Non Final Office Action dated Aug. 29, 2011", 2 pgs.

"New Zealand Application Serial No. 585697, Response filed Aug. 11, 2011 to Examination Report dated Jun. 3, 2010", 3 pgs.

* cited by examiner

SUBSTITUTED 4-{3-[6-AMINO-9-(3,4-DIHYDROXY-TETRAHYDRO-FURAN-2-YL)-9H-PURIN-2-YL]-PROP-2-YNYL}-PIPERIDINE-1-CARBOXYLIC ACID ESTERS AS $A_{2A}R$ AGONISTS

RELATED APPLICATION

This patent application claims the priority benefit of U.S. Provisional Patent Application Ser. No. 61/015,415 filed Dec. 20, 2007 and entitled "SUBSTITUTED 4-{3-[6-AMINO-9-(3,4-DIHYDROXY-TETRAHYDRO-FURAN-2-YL)-9H-PURIN-2-YL]-PROP-2-YNYL}-PIPERIDINE-1-CARBOXYLIC ACID ESTERS AS $A_{2A}R$ AGONISTS", the contents of which is incorporated herein by reference in its entirety.

STATEMENT OF GOVERNMENT RIGHTS

This invention was made with government support under United States Grant Nos. 1 R41 AR052960 and 1 R41 AI 071496-01 awarded by the National Institutes of Health. The government has certain rights in the invention.

FIELD OF THE INVENTION

The present invention relates to substituted 4-{3-[6-amino-9-(3,4-dihydroxy-tetrahydro-furan-2-yl)-9H-purin-2-yl]-prop-2-ynyl}-piperidine-1-carboxylic acid esters and pharmaceutical compositions that are selective agonists of $A_{2A}$ adenosine receptors (ARs). These compounds and compositions are useful as pharmaceutical agents.

BACKGROUND OF THE INVENTION

There has been progressive development of compounds that are more and more potent and/or selective as agonists of $A_{2A}$ adenosine receptors (AR) based on radioligand binding assays and physiological responses. For example, U.S. Pat. No. 6,232,297 to Linden, et al. describes compounds having the general formula:

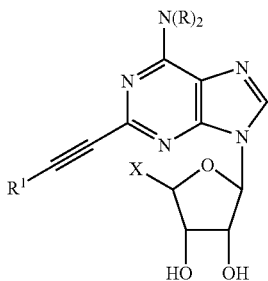

wherein each R can be H, X can be ethylaminocarbonyl and $R^1$ can be 4-methoxycarbonylcyclohexylmethyl (DWH-146e). These compounds are reported to be $A_{2A}$ agonists.

U.S. Pat. No. 7,214,665 to Linden, et al. describes compounds having the general formula:

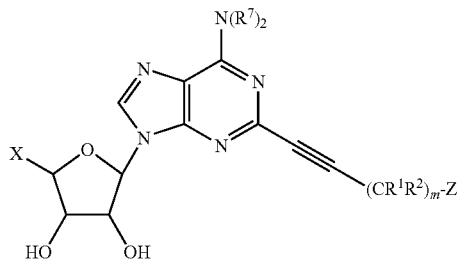

wherein $R^7$ can be H, X can be an ether or an amide, $CR^1R^2$ can be $CH_2$, and Z can be a heterocyclic ring. These compounds are reported to be $A_{2A}$ agonists.

U.S. Pat. Appl. No. 2006/004088 to Rieger, et al. describes compounds having the general formula:

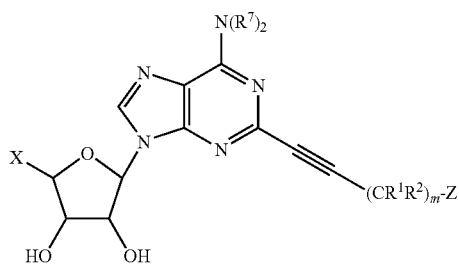

wherein $R^7$ can be H, X can be a cycloalkyl-substituted ether or amide, $CR^1R^2$ can be $CH_2$, and Z can be a heterocyclic ring. These compounds are reported to be $A_{2A}$ agonists.

U.S. Pat. Appl. No. 2007/0270373 to Rieger, et al. describes compounds having the general formula:

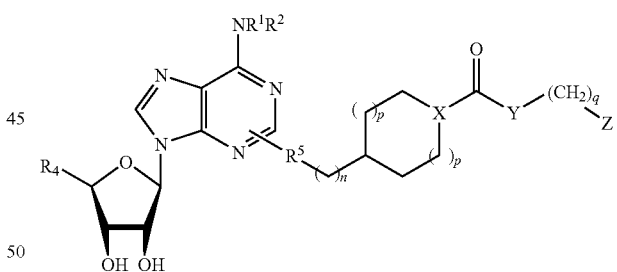

wherein $NR^1R^2$ can be $NH_2$, $R^4$ can be an ether or an amide, $R^5$ can be ethynyl, Y can be O or $NR^1$, and Z can be an aryl or heteroaryl. These compounds are reported to be $A_{2A}$ agonists.

Even in view of the above, a continuing need exists for $A_2$ adenosine receptor agonists useful for therapeutic applications.

SUMMARY OF THE INVENTION

The present invention provides substituted 4-{3-[6-amino-9-(3,4-dihydroxy-tetrahydro-furan-2-yl)-9H-purin-2-yl]-prop-2-ynyl}-piperidine-1-carboxylic acid esters or stereoisomers or pharmaceutically acceptable salts that act as agonists of $A_{2A}$ adenosine receptors.

One embodiment provides pharmaceutical compositions comprising a compound of the present invention or stereoisomer or a pharmaceutically acceptable salt thereof in combination with a pharmaceutically acceptable excipient.

Another embodiment provides novel methods of treatment and diagnosis with compounds and compositions of the present invention.

One embodiment provides novel compounds of the present invention for use in medical therapy.

Another embodiment provides the use of a novel compound of the present invention for the manufacture of a medicament for the treatment of a pathological condition or symptom in a mammal that the $A_{2A}$ receptor is implicated and for which agonism of the receptor provides therapeutic benefit.

These and other aspects have been accomplished in view of the discovery of substituted 4-{3-[6-amino-9-(3,4-dihydroxy-tetrahydro-furan-2-yl)-9H-purin-2-yl]-prop-2-ynyl}-piperidine-1-carboxylic acid esters described herein.

DETAILED DESCRIPTION OF THE INVENTION

The present invention provides novel substituted 4-{3-[6-amino-9-(3,4-dihydroxy-tetrahydro-furan-2-yl)-9H-purin-2-yl]-prop-2-ynyl}-piperidine-1-carboxylic acid esters that act as agonists at the adenosine $A_{2A}$ receptor, and methods for using the compounds in methods of treating diseases and conditions in which the $A_{2A}$ receptor is implicated and for which agonism of the receptor provides therapeutic benefit. The compounds may be used, for example, for the treatment of inflammatory activity in mammalian tissue, or for the treatment of sickle cell disease. The inflammatory tissue activity can be due to pathological agents or can be due to physical, chemical or thermal trauma, or the trauma of medical procedures, such as organ, tissue or cell transplantation, angioplasty (PCTA), inflammation following ischemia/reperfusion, or grafting. Compounds of the invention also may be used in conjunction with other anti-inflammatory treatments or in conjunction with anti-pathogenic agents.

One embodiment provides a novel compound of formula I or a stereoisomer or pharmaceutically acceptable salt thereof:

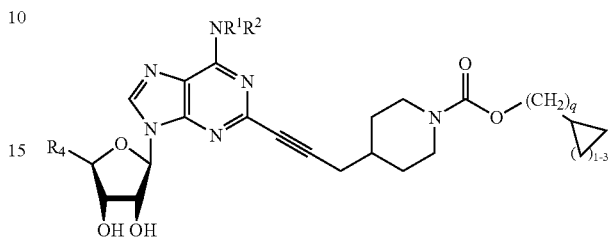

I wherein:
$R^1$ and $R^2$ independently are selected from H and $C_{1-3}$ alkyl;
$R^4$ is selected from $CH_2OR$ and $C(O)NRR$,
each R independently is selected from H, $C_{1-4}$ alkyl, cyclobutyl, and $(CH_2)_a$cyclopropyl;
a is selected from 0, 1, and 2;
q is selected from 1, 2, and 3.

Another embodiment provides a novel compound, wherein:
$R^1$ and $R^2$ are H;
$R^4$ is C(O)NRR;
each R independently is selected from H, $C_{1-4}$ alkyl, cyclopropyl, cyclobutyl, and —$CH_2$-cyclopropyl;
q is 1.

Another embodiment provides a novel compound, wherein: the compound is selected from:

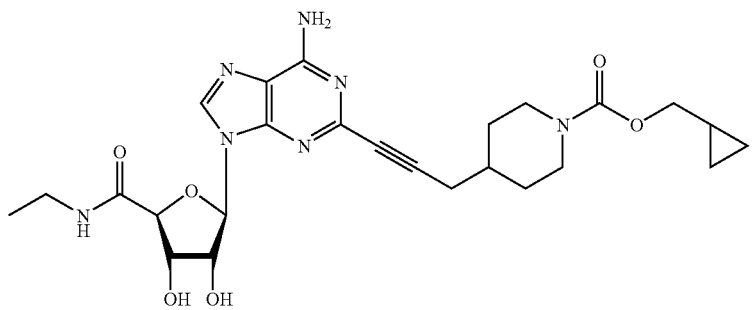

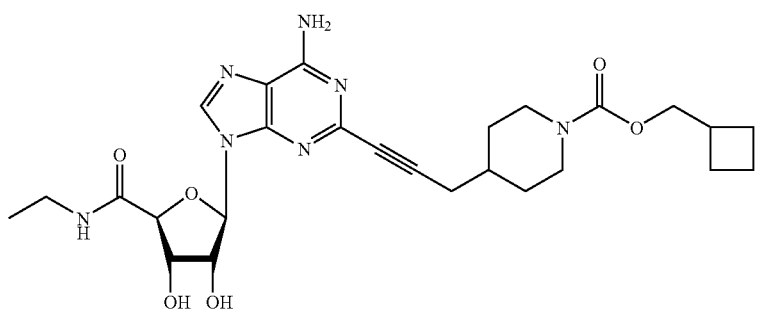

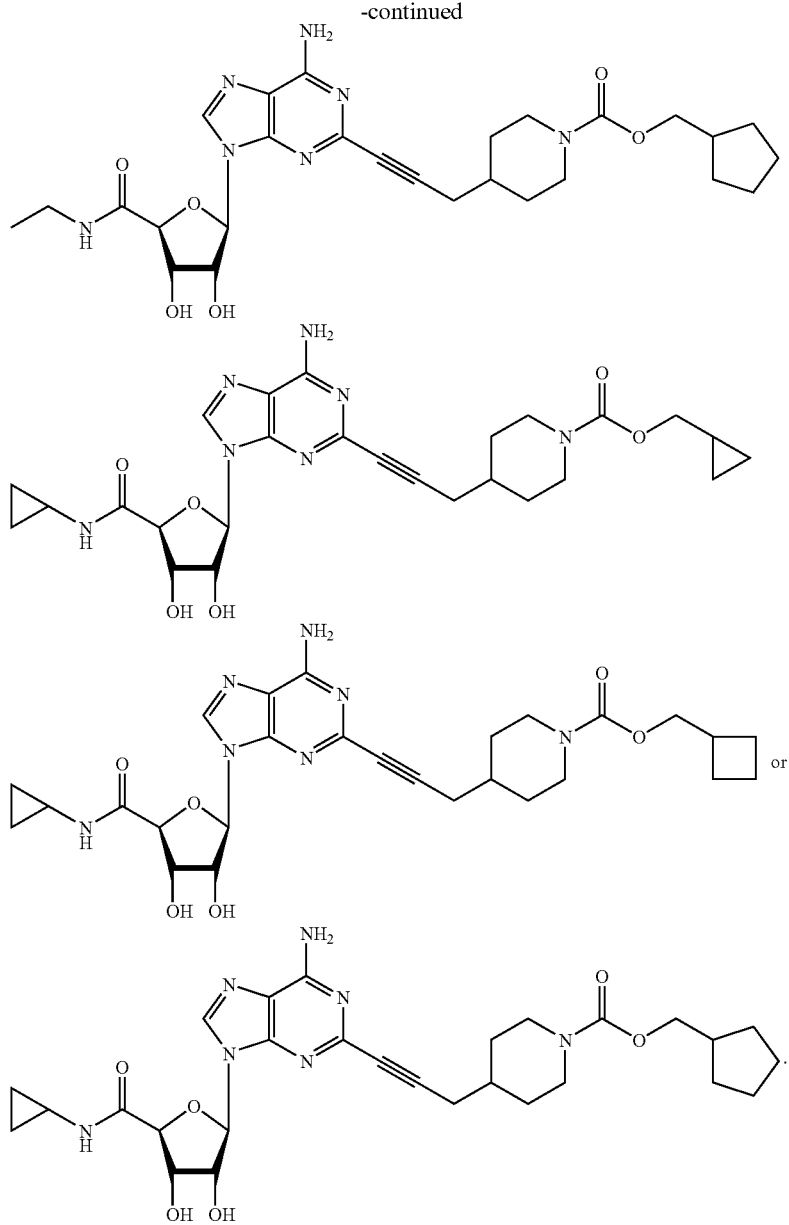

The invention provides a novel compound for use in medical therapy, preferably for use in treating inflammation or protecting mammalian tissue from inflammation such as an inflammatory response, e.g., resulting from allergy, trauma or ischemia/reperfusion injury, as well as the use of a compound of the present invention for the manufacture of a medicament for the treatment of an inflammatory response due to a pathological condition or symptom in a mammal which is associated with inflammation.

Mammal or subject includes human, equine, porcine, canine, and feline.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

One embodiment includes the use of a combination of these compounds with at least one anti-inflammatory compound. An example of such a compound is a type IV phosphodiesterase inhibitor. The combination can be used to cause synergistic decreases in the inflammatory response mediated by leukocytes.

Another embodiment provides a pharmaceutical composition comprising an effective amount of a compound of the present invention, or a pharmaceutically acceptable salt thereof, in combination with a pharmaceutically acceptable diluent or carrier, and optionally, in combination with an anti-inflammatory compound. The composition can be presented as a unit dosage form. The carrier can be a liquid carrier. The composition can be adapted for oral, intravenous, ocular, parenteral, aerosol or transdermal administration.

The compositions may further include a Type IV phosphodiesterase inhibitor, or another anti-inflammatory compound (e.g., other than a PDE inhibitor). The Type IV phosphodiesterase inhibitor may be, for example, rolipram, cilomilast, or roflumilast.

Additionally, the invention provides a therapeutic method for treating a pathological condition or symptom in a mammal where the activity of $A_{2A}$ adenosine receptors is implicated and agonism of said receptors is desired, comprising administering to a mammal in need of such therapy, an effective amount of a compound of the present invention, or a pharmaceutically acceptable salt thereof. It is believed that activation of $A_{2A}$ adenosine receptors inhibits inflammation by affecting neutrophils, mast cells, monocytes/macrophages, platelets T-cells and/or eosinophils. Inhibition of these inflammatory cells results in tissue protection following tissue insults.

In addition, the present invention provides a therapeutic method for treating biological diseases that includes the administration of an effective amount of a suitable antibiotic agent, antifungal agent or antiviral agent in conjunction with an $A_{2A}$ adenosine receptor agonist. If no anti-pathogenic agent is known the $A_{2A}$ agonist can be used alone to reduce inflammation, as may occur during infection with antibiotic resistant bacteria, or certain viruses such as those that cause SARS or Ebola. Optionally, the method includes administration of a type IV PDE inhibitor. The $A_{2A}$ adenosine receptor agonist can provide adjunctive therapy for treatment conditions such as, inflammation, caused by sepsis, for example, human uremic syndrome when administered with antibiotics in the treatment of bio-terrorism weapons, such as anthrax, tularemia, *Escherichia coli*, plague and the like. The present invention also provides adjunctive therapy for treatment of lethal bacterial, fungal and viral infections such as anthrax, tularemia, *escherichia* and plague comprising administration of an antibacterial agent, an antifungal agent or an antiviral agent in conjunction with selective $A_{2A}$ adenosine receptor agonists.

The present invention provides a therapeutic method for treating biological diseases that provoke inflammation either alone or in combination with a disease killing medicine. These include bacteria in combination with antibiotics, including but not limited to bacteria that cause anthrax, tularemia, plague, lyme disease and anthrax. Also included are viruses including but not limited to those that cause RSV, severe acute respiratory syndrome (SARS), influenza and Ebola with or without anti-viral therapy. Also included are yeast and fungal infections with or without anti-yeast or antifungal agents.

The antibacterial agent, antifungal agent or antiviral agent can be co-administered (e.g., simultaneously) with the $A_{2A}$ adenosine receptor agonist or they can be administered either simultaneously or as a mixture or they can be administered subsequently. The subsequent administration of the $A_{2A}$ adenosine receptor agonists can be prior to the agent, within minutes or up to about 48 hours after the administration of the agent. Preferably the administration of the $A_{2A}$ adenosine receptor agonists will be within about 24 hours and more preferably within about 12 hours.

The method of the invention will also be useful for treating patients with sepsis, severe sepsis, and potentially, the systemic inflammatory response syndrome, in addition to septic shock. The $A_{2A}$ adenosine receptor agonists exert multiple anti-inflammatory effects early in the inflammatory cascade, and thus a short course of such agonists can produce profound benefit in serious, life-threatening infectious and inflammatory disorders of humans, including inhalational anthrax, tularemia, *escherichia* and plague.

The anti-inflammatory effect of $A_{2A}$ receptor agonists has been documented in vivo, in experimental models of meningitis, peritonitis and arthritis. The potentially fatal syndrome of bacterial sepsis is an increasingly common problem in acute care units. Sepsis and septic shock, now the eleventh leading cause of death in the United States, are increasing in frequency. Current estimates indicate that about 900,000 new cases of sepsis (approximately 60% Gram negative) occur in the United States annually with an estimated crude mortality rate of 35%. Furthermore, the mortality rate, as assessed in recent clinical trials, is approximately 25%, while approximately 10% of patients die from their underlying disease. Shock develops in approximately 200,000 cases annually with an attributable mortality rate of 46% (92,000 deaths). Sepsis accounts for an estimated $5-10 billion annually in health care expenditures. It is now widely appreciated that among hospitalized patients in non-coronary intensive care units, sepsis is the most common cause of death. Sepsis syndrome is a public health problem of major importance. $A_{2A}AR$ agonists have use as a new and unique adjunctive therapeutic approach to reduce morbidity and mortality. It is believed that this treatment will improve the outcome in systemic anthrax, tularemia, *escherichia* and plague.

The agonists of $A_{2A}$ adenosine receptors of the invention can inhibit neutrophil, macrophage and T cell activation and thereby reduce inflammation caused by bacterial and viral infections. The compounds, in conjunction with antibiotics or antiviral agents can prevent or reduce mortality caused by sepsis or hemolytic uremic syndrome or other inflammatory conditions. The effects of adenosine $A_{2A}$ agonists are enhanced by type IV phosphodiesterase inhibitors such as rolipram.

The invention also provides a compound of the present invention for use in medical therapy (e.g., for use as an adjunct in the treatment of potentially lethal bacterial infections, such as, anthrax, tularemia, *Escherichia*, plague, or other bacterial or viral infections, and treatment of systemic intoxification caused by bacterial and/or viral infections, as well as the use of a compound of the present invention for the manufacture of a medicament for reducing inflammation caused by the bacteria or virus or the treatment thereof in a mammal, such as a human. The compounds of the invention are also useful for treatment of systemic intoxification wherein the bacterial or viral agents cause inflammation either directly or as a result of treatment, e.g., with an antibiotic or antiviral agent.

Sepsis is a severe illness caused by overwhelming infection of the bloodstream by toxin-producing bacteria or viruses. The infection, which can manifest as inflammation, can be caused by the bacteria or virus pathogens directly or from the treatment thereof, i.e., the death of the pathogens due to treatment with antibacterial or antiviral agents. Sepsis also can be viewed as the body's response to an infection. The infection can be caused by microorganisms or "germs" (usually bacteria) invade the body, can be limited to a particular body region (e.g., a tooth abscess) or can be widespread in the bloodstream (often referred to as "septicemia" or "blood poisoning").

The systemic intoxification or inflammatory shock is often referred to as Septic shock; Bacteremic shock; Endotoxic shock; Septicemic shock; or Warm shock.

Septic shock is a serious, abnormal condition that occurs when an overwhelming infection leads to low blood pressure and low blood flow. Vital organs, such as the brain, heart, kidneys, and liver may not function properly or may fail. Septic shock occurs most often in the very old and the very young. It also occurs in people with underlying illnesses. Any bacterial organism can cause septic shock. Fungi and viruses may also cause this condition. Toxins released by the bacteria, fungi or viruses may cause direct tissue damage, and may lead to low blood pressure and/or poor organ function. These toxins can also produce a vigorous inflammatory response from the body, which contributes to septic shock.

In another aspect, the present invention also provides a method to treat severe acute respiratory syndrome (SARS), comprising administering to a mammal in need of said therapy, an effective anti-inflammatory amount of an agonists of $A_{2A}$ adenosine receptor, optionally with a PDE-IV inhibitor, such as, rolipram.

The invention also provides methods of treating sickle cell disease by administering the $A_{2A}$ agonists described herein to a subject suffering from sickle cell disease.

The present invention provides compounds and methods of their use for detecting the presence of, and assessing the severity of, coronary artery stenoses in a mammal, such as a human or domestic animal. Preferably, the compounds of the invention are used as pharmacological stress-inducing agents or stressors that are useful in pharmacological stress imaging for the detection and assessment of coronary artery disease. The specific compounds of the invention useful as stress-inducing agents are potent and selective at $A_{2A}$ adenosine receptors, but are also short-acting, so that they are rapidly cleared by the body following the imaging process.

Thus, the present invention provides a method for detecting the presence and severity of coronary artery stenoses in a mammal, such as a human subject, comprising (1) administering an amount of one or more compounds of the present invention and (2) performing a technique on said mammal to detect and/or determine the severity of said coronary artery stenoses.

A compound of the present invention is provided for use in medical diagnostic procedures, preferably for use in detecting the presence of, and assessing the severity of, coronary artery stenoses in a human subject. The present invention provides the use of a compound of the present invention for the manufacture of a pharmacologic vasodilator agent which could be used with clinical perfusion imaging techniques for diagnosing and assessing the extent of coronary artery disease. Preferred perfusion imaging techniques are planar or single photon emission computed tomography (SPECT), gamma camera scintigraphy, positron emission tomography (PET), nuclear magnetic resonance (NMR) imaging, magnetic resonance imaging (MRI), perfusion contrast echocardiography, digital subtraction angiography (DSA) and ultrafast X-ray computed tomography (CINE CT).

A pharmaceutical composition comprising an effective amount of the compound of the present invention, or a pharmaceutically acceptable salt thereof, in combination with a pharmaceutically acceptable diluent or carrier is also provided. Preferably, the composition is presented as a unit dosage form, and can be adapted for parenteral, e.g., intravenous infusion.

The following definitions are used, unless otherwise described.

Halo is fluoro, chloro, bromo, or iodo.

Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to.

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(Y) wherein Y is absent or is H, O, ($C_1$-$C_8$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

Heteroaryl encompasses a monocyclic aromatic ring having five or six ring atoms consisting of carbon and 1-4 heteroatoms each selected from the group consisting of non-peroxide oxygen, sulfur, and N(X) wherein X is absent, is H, O, ($C_1$-$C_4$)alkyl, phenyl or benzyl, or is a substituent defined elsewhere. Heteroaryl also encompasses a radical of an ortho-fused bicyclic heterocycle of 8-10 ring atoms, particularly a benz-derivative or one derived by fusing a propylene, trimethylene, or tetramethylene diradical thereto. Only one ring of the bicyclic heteroaryl need be aromatic.

The term "heterocycle" generally represents a non aromatic heterocyclic group, having from 3 to about 10 ring atoms, which can be saturated or partially unsaturated, containing at least one heteroatom (e.g., 1, 2, or 3) selected from the group consisting of oxygen, nitrogen, and sulfur. Specific, "heterocycle" groups include monocyclic, bicyclic, or tricyclic groups containing one or more heteroatoms selected from the group consisting of oxygen, nitrogen, and sulfur. A "heterocycle" group also can include one or more oxo groups (=O) attached to a ring atom. Non-limiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term carbocyclic biaryl refers to ortho-fused bicyclic moieties, typically containing 10 carbon atoms. An example is naphthalene. The term heterocyclic biaryl as used herein refers to ortho-fused bicyclic moieties containing 1-4 heteroatoms. Examples include indoles, isoindoles, quinolines, isoquinolines, benzofurans, isobenzofurans, benzothiophenes, benzo[c]thiophenes, benzimidazoles, purines, indazoles, benzoxazole, benzisoxazole, benzothiazole, quinoxalines, quinazolines, cinnolines, and the like.

The point of attachment of either the carbocyclic or heterocyclic biaryl can be to any ring atom permitted by the valency of that atom.

Specific values listed below for radicals, substituents, and ranges, are for illustration only; they do not exclude other defined values or other values within defined ranges for the radicals and substituents.

Carbon chains and their optionally substituted counterparts can be in any branched chain form permitted by the valencies and steric requirements of the atoms. Specifically, ($C_1$-$C_8$)alkyl can be methyl, ethyl, propyl, isopropyl, butyl, iso-butyl, sec-butyl, tert-butyl, pentyl, 3-pentyl, neopentyl, hexyl, heptyl, octyl, and the like, in any branched chain form.

As used herein, the term "cycloalkyl" encompasses bicycloalkyl (norbornyl, 2.2.2-bicyclooctyl, etc.) and tricycloalkyl (adamantyl, etc.), optionally comprising 1-2 N, O or S. Cycloalkyl also encompasses (cycloalkyl)alkyl. Thus, ($C_3$-$C_6$)cycloalkyl can be cyclopropyl, cyclobutyl, cyclopentyl, cyclohexyl and the like. ($C_1$-$C_8$)alkoxy can be methoxy, ethoxy, propoxy, isopropoxy, butoxy, iso-butoxy, sec-butoxy, pentoxy, 3-pentoxy, or hexyloxy, in any branched chain form.

$(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

$(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl.

$(C_1-C_6)$alkoxycarbonyl$(CO_2R^2)$ can be methoxycarbonyl, ethoxycarbonyl, propoxycarbonyl, isopropoxycarbonyl, butoxycarbonyl, pentoxycarbonyl, or hexyloxycarbonyl.

$(C_1-C_6)$alkylthio can be methylthio, ethylthio, propylthio, isopropylthio, butylthio, isobutylthio, pentylthio, or hexylthio.

$(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, puridyl (or its N-oxide), thienyl, pyrimidinyl (or its N-oxide), indolyl, isoquinolyl (or its N-oxide) or quinolyl (or its N-oxide).

The term "alkylene" refers to a divalent straight or branched hydrocarbon chain (e.g. ethylene —$CH_2CH_2$—).

The term "aryl$(C_1-C_8)$alkylene" for example includes benzyl, phenethyl, 3-phenylpropyl, naphthylmethyl and the like.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein the term "in conjunction with" refers to co-administration of an anti-rejection agent with the $A_{2A}$ adenosine receptor agonist. The co-administration of an agent and an $A_{2A}$ adenosine receptor agonists includes administration of the agent and agonist either simultaneously, as a mixture, or sequentially. The sequential administration of the $A_{2A}$ adenosine receptor agonists can be prior to administration of the agent, within minutes or up to about 48 hours either before the administration of the agent. The $A_{2A}$ adenosine receptor agonists can also be administered after the agent. Preferably the administration of the $A_{2A}$ adenosine receptor agonists will be within about 24 hours and more preferably within about 12 hours.

The carbon atom content of various hydrocarbon-containing moieties is indicated by a prefix designating the minimum and maximum number of carbon atoms in the moiety, i.e., the prefix $C_i-C_j$ indicates a moiety of the integer "i" to the integer "j" carbon atoms, inclusive. Thus, for example, $(C_1-C_8)$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

It will be appreciated by those skilled in the art that the compounds of the present invention have more than one chiral center and may be isolated in optically active and racemic forms. Preferably, the riboside moiety of the present invention is derived from D-ribose. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Among the inflammatory responses that can be treated (including treated prophylactically) with a compound of the present invention, optionally with a Type IV PDE inhibitor, are inflammation due to: (a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis; (b) allergic diseases such as asthma, hay fever, rhinitis, poison ivy, vernal conjunctivitis and other eosinophil-mediated conditions; (c) skin diseases such as psoriasis, contact dermatitis, eczema, infectious skin ulcers, healing of open wounds, cellulitis; (d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), chronic obstructive pulmonary disease (COPD), lyme disease, HIV infection, (TNFα-enhanced HIV replication, TNFα inhibition of reverse transcriptase inhibitor activity); (e) wasting diseases: cachexia secondary to cancer and HIV; (f) organ, tissue or cell transplantation (e.g., bone marrow, cornea, kidney, lung, liver, heart, skin, pancreatic islets) including transplant rejection, and graft versus host disease; (g) adverse effects from drug therapy, including adverse effects from amphotericin B treatment, adverse effects from immunosuppressive therapy, e.g., interleukin-2 treatment, adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression; (h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes; (i) dialysis, including pericarditis, due to peritoneal dialysis; (j) gout; and (k) chemical or thermal trauma due to burns, acid, alkali and the like.

Additional diseases include equine disorders such as laminitis and founder's disease.

Of particular interest and efficacy is the use of the present compounds to limit inflammatory responses where the ischemia/reperfusion injury is caused by angioplasty or throbolysis. Also of particular interest and efficacy is the use of the present compounds to limit inflammatory responses due to organ, tissue or cell transplantation, i.e., the transplantation of allogeneic or xenogeneic tissue into a mammalian recipient, autoimmune diseases and inflammatory conditions due to circulatory pathologies and the treatment thereof, including angioplasty, stent placement, shunt placement or grafting. Unexpectedly, it is found that administration of one or more compounds of the present invention is effective after the onset of the inflammatory response, e.g., after the subject is afflicted with a pathology or trauma that initiates an inflammatory response.

Tissue or cells comprising ligand bound receptor sites can be used to measure the selectively of test compounds for specific receptor subtypes, the amount of bioactive compound in blood or other physiological fluids, or can be used as a tool to identify potential therapeutic agents for the treatment of diseases or conditions associated with receptor site activation, by contacting said agents with said ligand-receptor complexes, and measuring the extent of displacement of the ligand and/or binding of the agent, or the cellular response to said agent (e.g., cAMP accumulation).

The following abbreviations have been used herein:

| | |
|---|---|
| 2-Aas | 2-alkynyladenosines; |
| $^{125}$I-ABA | $N^6$-(4-amino-3-$^{125}$iodo-benzyl)adenosine |
| APCI | Atmospheric pressure chemical ionization |
| CCPA | 2-chloro-$N^6$-cyclopentyladenosine; |
| Cl-IB-MECA | $N^6$-3-iodo-2-chlorobenzyladenosine-5'-N-methyl-uronamide; |
| CPA | $N^6$-cyclopentyladenosine |
| DMF | dimethylformamide |
| DMSO | dimethylsulfoxide |
| DMSO-$d_6$ | deuterated dimethylsulfoxide |
| EtOAc | ethyl acetate |
| eq | equivalent |
| GPCR | G protein coupled receptor; hA$_{2A}$AR, Recombinant human A$_{2A}$ adenosine receptor; |
| IADO | 2-Iodoadenosine |
| $^{125}$I-APE, | 2-[2-(4-amino-3-[$^{125}$I]iodophenyl)ethylamino]-adenosine; |
| NECA | 5'-N-ethylcarboxamidoadenosine; |
| IB-MECA | $N^6$-3-iodobenzyladenosine-5'-N-methyluronamide; |
| 2-Iodoadenosine | 5-(6-amino-2-iodo-purin-9-yl)-3,4-dihydroxytetra-hydro-furan-2carboxylic acid ethylamide |
| HPLC | high-performance liquid chromatography |
| HRMS | high-resolution mass spectrometry |
| $^{125}$I-ZM241385, | $^{125}$I-4-(2-[7-amino-2-[2-furyl][1,2,4]triazolo[2,3-α]-[1,3,5]triazin-5-yl-amino]ethyl)phenol; |
| INECA | 2-iodo-N-ethylcarboxamidoadenosine |
| LC/MS | liquid chromatography/mass spectrometry |
| m.p. | melting point |
| MHz | megahertz |
| MRS 1220, | N-(9-chloro-2-furan-2-yl-[1,2,4]triazolo[1,5-c]-quinazolin-5-yl)-2-phenylacetamide; |
| MS | mass spectrometry |
| NECA | N-ethylcarboxamidoadenosine |
| NMR | nuclear magnetic resonance |
| RP-HPLC | reverse phase high-performance liquid chromatography |
| TBAF | tetrabutylammonium fluoride |
| TBS | tert-butyldimethylsilyl |
| TBDMSCl | tert-butyldimethylsilylchloride |
| TEA | triethylamine |
| TFA | trifluoroacetic acid |

-continued

| | |
|---|---|
| THF | tetrahydrofuan |
| TLC | thin layer chromatography |
| p-TSOH | para-toluenesulfonic acid |
| XAC | 8-(4-((2-aminoethyl)aminocarbonyl-methyloxy)-phenyl)-1-3-dipropylxanthine. |

Specific Type IV phosphodiesterase (PDE) inhibitors useful in practicing the instant invention include racemic and optically active 4-(polyalkoxyphenyl)-2-pyrrolidones as disclosed and described in U.S. Pat. No. 4,193,926. Rolipram is an example of a suitable Type IV PDE.

The present invention further provides pharmaceutical compositions that include a compound of the present invention in combination with one of more members selected from the group consisting of the following: (a) Leukotriene biosynthesis inhibitors, 5-lipoxygenase (5-LO) inhibitors, and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2-alkylsulfonamid-es of Formula (5.2.8); 2,6-di-tert-butylphenol hydrazones of Formula (5.2.10); Zeneca ZD-2138 of Formula (5.2.11); SB-210661 of Formula (5.2.12); pyridinyl-substituted 2-cyanonaphtha-lene compound L-739,010; 2-cyanoquinoline compound L-746,530; indole and quinoline, compounds MK-591, MK-886, and BAY x 1005; (b) Receptor antagonists for leukotrienes LTB4, LTC4, LTD4, and LTE4 selected from the group consisting of phenothiazin-3-one compound L-651, 392; amidino compound CGS-25019c; benzoxazolamine compound ontazolast; benzenecarboximidamide compound BIIL 284/260; compounds zafirlukast, ablukast, montelukast, pranlukast, verlukast (MK-679), RG-12525, Ro-245913, iralukast (CGP 45715A), and BAY x 7195; (d) 5-Lipoxygenase (5-LO) inhibitors; and 5-lipoxygenase activating protein (FLAP) antagonists; (e) Dual inhibitors of 5-lipoxygenase (5-LO) and antagonists of platelet activating factor (PAF); (f) Theophylline and aminophylline; (g) COX-1 inhibitors (NSAIDs); and nitric oxide NSAIDs; (h) COX-2 selective inhibitor rofecoxib; (i) Inhaled glucocorticoids with reduced systemic side effects selected from the group consisting of prednisone, predniso lone, flunisolide, triamcinolone acetonide, beclomethasone dipropionate, budesonide, fluticasone propionate, and mometasone furoate; (j) Platelet activating factor (PAF) antagonists; (k) Monoclonal antibodies active against endogenous inflammatory entities; (l) Anti-tumor necrosis factor (TNFα) agents selected from the group consisting of etanercept, infliximab, and D2E7; (m) Adhesion molecule inhibitors including VLA-4 antagonists; (n) Immunosuppressive agents selected from the group consisting of cyclosporine, azathioprine, and methotrexate; or (O) anti-gout agents selected from the group consisting of colchicines.

Examples of pharmaceutically acceptable salts are organic acid addition salts formed with acids that form a physiological acceptable anion, for example, tosylate, methanesulfonate, malate, acetate, citrate, malonate, tartrate, succinate, benzoate, ascorbate, α-ketoglutarate, and α-glycerophosphate. Suitable inorganic salts may also be formed, including hydroCl, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium or lithium) or alkaline earth metal (for example calcium) salts of carboxylic acids can also be made.

The compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain: binders, such as gum tragacanth, acacia, corn starch or gelatin; excipients, such as dicalcium phosphate; a disintegrating agent, such as corn starch, potato starch, alginic acid and the like; a lubricant, such as magnesium stearate; and a sweetening agent, such as sucrose, fructose, lactose or aspartame or a flavoring agent, such as peppermint, oil of wintergreen, or cherry flavoring. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients as enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid, a liquid or in a dermatological patch.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions, which can be used to deliver the compounds of the present invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949. Useful dosages of Type IV PDE inhibitors are known to the art. For example, see, U.S. Pat. No. 5,877,180, Col. 12.

Generally, the concentration of the compound(s) of the present invention in a liquid composition, such as a lotion, will be from about 0.1-25% wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 µg/kg, e.g., from about 10 to about 75 µg/kg of body weight per day, such as 3 to about 50 µg per kilogram body weight of the recipient per day, preferably in the range of 6 to 90 µg/kg/day, most preferably in the range of 15 to 60 µg/kg/day.

The compound is conveniently administered in unit dosage form; for example, containing 5 to 1000 µg, conveniently 10 to 750 µg, most conveniently, 50 to 500 µg of active ingredient per unit dosage form.

Ideally, the active ingredient should be administered to achieve peak plasma concentrations of the active compound of from about 0.1 to about 10 nM, preferably, about 0.2 to 10 nM, most preferably, about 0.5 to about 5 nM. This may be achieved, for example, by the intravenous injection of a 0.05 to 5% solution of the active ingredient, optionally in saline, or orally administered as a bolus containing about 1-100 µg of the active ingredient. Desirable blood levels may be maintained by continuous infusion to provide about 0.01-5.0 µg/kg/hr or by intermittent infusions containing about 0.4-15 µg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. For example, it is desirable to administer the present compositions intravenously over an extended period of time following the insult that gives rise to inflammation.

The ability of a given compound of the invention to act as an $A_{2A}$ adenosine receptor agonist may be determined using pharmacological models which are well known to the art, or using tests described below.

The present compounds and compositions containing them are administered as pharmacological stressors and used in conjunction with any one of several noninvasive diagnostic procedures to measure aspects of myocardial perfusion. For example, intravenous adenosine may be used in conjunction with thallium-201 myocardial perfusion imaging to assess the severity of myocardial ischemia. In this case, any one of several different radiopharmaceuticals may be substituted for thallium-201 (e.g., technetium-99m-labeled radiopharmaceuticals (ie: Tc-99m-sestamibi, Tc-99m-teboroxime), iodine-123-labeled radiopharmaceuticals such as I-123-IPPA or BMIPP, rubidium-82, nitrogen-13, etc.). Similarly, one of the present compounds may be administered as a pharmacological stressor in conjunction with radionuclide ventriculography to assess the severity of myocardial contractile dysfunction. In this case, radionuclide ventriculographic studies may be first pass or gated equilibrium studies of the right and/or left ventricle. Similarly, a compound of the present invention may be administered as a pharmacological stressor in conjunction with echocardiography to assess the presence of regional wall motion abnormalities. Similarly, the active compound may be administered as a pharmacological stressor in conjunction with invasive measurements of coronary blood flow such as by intracardiac catheter to assess the functional significance of stenotic coronary vessels.

There also is provided a method to diagnose myocardial perfusion abnormalities in a mammal comprising: (a) parenterally administering to said mammal an amount of a compound or composition as described above; and (b) performing a technique on the mammal to detect the presence of coronary artery stenoses, assess the severity of coronary artery stenoses or both. The myocardial dysfunction may be, for example, coronary artery disease, ventricular dysfunction and differences in blood flow through disease-free coronary vessels and/or stenotic coronary vessels. The technique to detect the presence and assess the severity of coronary artery disease may be, for example, radiopharmaceutical myocardial perfusion imaging, ventricular function imaging, or techniques for measuring coronary blood flow velocity. The radiopharmaceutical myocardial perfusion imaging may be, for example, planar scintigraphy, single photon emission computed tomography (SPECT), positron emission tomography (PET), nuclear magnetic resonance (NMR) imaging, perfusion contrast echocardiography, digital subtraction angiography (DSA) and ultrafast X-ray computed tomography (CINE CT). A radiopharmaceutical agent may be used in conjunction with the radiopharmaceutical myocardial perfusion imaging, and the radiopharmaceutical agent may comprise, for example, a radionuclide selected from the group consisting of thallium-201, technetium-99m, nitrogen-13, rubidium-82, iodine-123 and oxygen-15. When the radiopharmaceutical myocardial perfusion imaging is scintigraphy, the radiopharmaceutical agent may be thallium-201. The ventricular function imaging technique may be, for example, echocardiography, contrast ventriculography or radionuclide ventriculography. The method for measuring coronary blood flow velocity may be, for example, doppler flow catheter, digital subtraction angiography and radiopharmaceutical imaging techniques. These methods of diagnosis may also comprise the steps of: (a) administering to the human by intravenous infusion or by bolus injection an amount of a compound or composition as described above to provide coronary artery dilation; (b) administering a radiopharmaceutical agent comprising thallium-201 or technetium-99m to the human; and (c) performing the scintigraphy on the human in order to detect the presence and assess the severity of coronary artery disease. The radiopharmaceutical agent may be, for example, Tc-99m-sestamibi.

The method typically involves the administration of one or more compounds of the present invention by intravenous infusion in doses which are effective to provide coronary artery dilation (approximately 0.25-500, preferably 1-250 mcg/kg/min). However, its use in the invasive setting may involve the intracoronary administration of the drug in bolus doses of 0.5-50 mcg.

Preferred methods comprise the use of a compound of the present invention as a substitute for exercise in conjunction with myocardial perfusion imaging to detect the presence and/or assess the severity of coronary artery disease in humans wherein myocardial perfusion imaging is performed by any one of several techniques including radiopharmaceutical myocardial perfusion imaging using planar scintigraphy or single photon emission computed tomography (SPECT), positron emission tomography (PET), nuclear magnetic resonance (NMR) imaging, perfusion contrast echocardiography, digital subtraction angiography (DSA), or ultrafast X-ray computed tomography (CINE CT).

A method is also provided comprising the use of a compound of the present invention as a substitute for exercise in conjunction with imaging to detect the presence and/or assess the severity of ischemic ventricular dysfunction in humans wherein ischemic ventricular dysfunction is measured by any one of several imaging techniques including echocardiography, contrast ventriculography, or radionuclide ventriculography. The myocardial dysfunction can be coronary artery disease, ventricular dysfunction, differences in blood flow through disease-free coronary vessels and stenotic coronary vessels and the like A method is also provided comprising the use of a compound of the present invention as a coronary hyperemic agent in conjunction with means for measuring coronary blood flow velocity to assess the vasodilatory capacity (reserve capacity) of coronary arteries in humans wherein coronary blood flow velocity is measured by any one of several techniques including Doppler flow catheter or digital subtraction angiography.

The invention will be further described by reference to the following detailed examples, which are given for illustration of the invention, and are not intended to be limiting thereof.

EXAMPLES

Nuclear magnetic resonance spectra for proton ($^1$H NMR) were recorded on a 300 MHz Varian Gemini 2000 (or similar instrument) spectrophotometer. The chemical shift values are expressed in ppm (parts per million) relative to tetramethylsilane. For data reporting, s=singlet, d=doublet, t=triplet, q=quartet, and m=multiplet. Mass spectra were measured on a Finnigan LCQ Advantage. Analytical HPLC was done on a Shimazdu LC10 or LC20 Systemtimes. 150 mm as described below. Preparative HPLC was performed on a Shimadzu Discovery HPLC with a Shim-pack VP-ODS C18 (20×100 mm) column operated at room temperature. Compounds were eluted at 30 mL/min with a gradient 20-80% of water (containing 0.1% TFA) to methanol over 15 minutes with UV detection at 254 nm using a SPD10A VP Tunable detector. All final compounds presented here were determined to be greater than 98% pure by HPLC. Flash chromatography was performed on Silicyle 60A gel (230-400 mesh) or using reusable chromatography columns and system from RT Scientific, Manchester N.H. All reactions were done under a nitrogen atmosphere in flame-dried glassware unless otherwise stated.

Example 1

4-{3-[6-Amino-9-(5-cyclopropylcarbamoyl-3,4-dihydroxy-tetrahydro-furan-2-yl)-9H-purin-2-yl]-prop-2-ynyl}-piperidine-1-carboxylic acid cyclobutyl ester

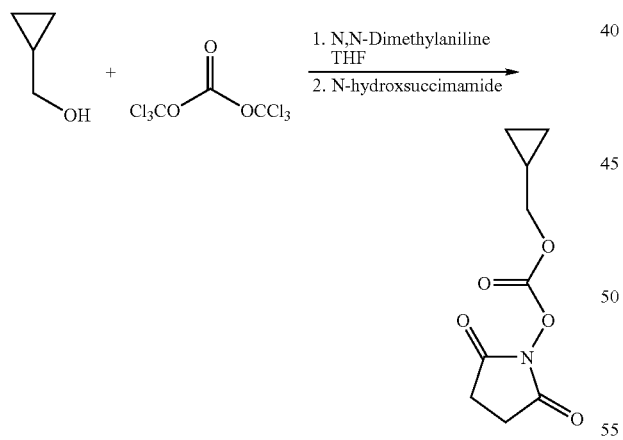

To triphosgene (0.34 eq) stirring in THF at 0° C. under inert atmosphere, the alcohol (1.0 eq) and dimethylaniline (1.1 eq) are added slowly as a solution in dry THF. After ten minutes, the reaction is warmed to room temperature and stirred for an additional 3 h. Dry DCM is then added and the mixture is poured slowly into a solution of N-hydroxysuccinamide (1.3 eq) in dry DCM at 0° C. The reaction is slowly warmed to room temperature and stirred overnight. Water is added to the mixture and after stirring for an additional 3 h, the solution is diluted with EtOAc. The organic layer is washed 3 times with water, once with brine, then dried (MgSO$_4$) and concentrated. The resulting oil (which may be a mixture of the carbonate and symmetrical anhydride) was taken directly onto the next step.

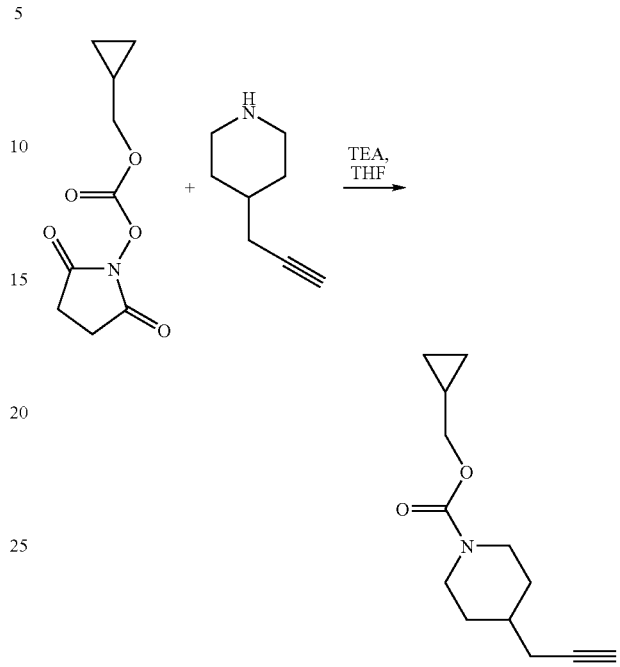

The piperidine derivative (0.75 eq) is dissolved in dry THF and TEA (excess) is added slowly at room temperature under inert atmosphere. The carbonate compound (1.0 eq) is diluted with THF and added dropwise to the piperidine solution. The mixture is stirred for 24 h then concentrated for application to silica gel chromatography (gradient starting at 100% hexanes up to 80% DCM in hexanes). The resulting oil (~60% yield) is stored at 4° C. until further use.

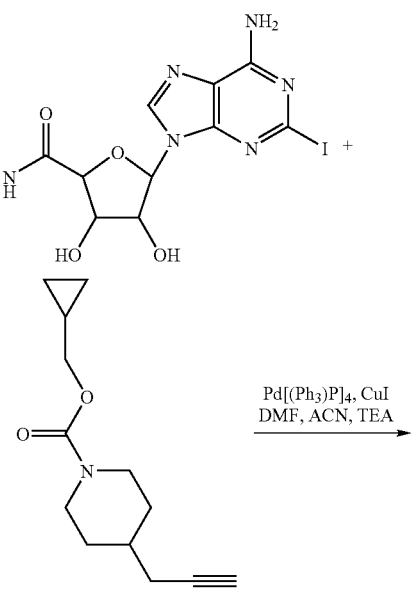

-continued

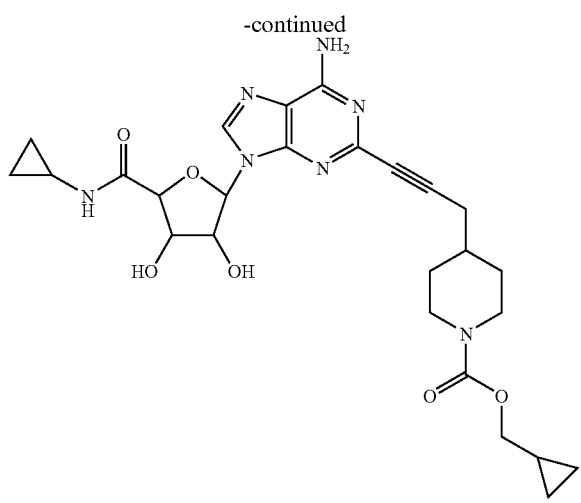

The iodo derivative (1.0 eq) is dissolved in a solution of DMF:ACN:TEA 5:5:1 (all solvent vigorously degassed) and stirred at room temperature under inert atmosphere. Palladium catalyst (~5 mol %) and copper (I) iodide (1.05 eq) are added followed by the alkyne derivative (4.0 eq). The resulting dark solution is stirred overnight then concentrated for application to silica gel chromatography (gradient starting at 100% DCM up to 10% MeOH in DCM). The resulting oil was further purified by preparative HPLC to obtain an off white solid (~30% yield).

$^1$H NMR (DDMSO) δ 8.57 (s, 1H), 8.29 (s, 1H), 7.52 (s, 2H), 5.98 (d, 1H, J=6.9), 5.68 (dd, 2H, J=22.5, 4.8), 4.64 (q, 1H, J=2.1), 4.30 (d, 1H, J=2.1), 4.21 (m, 1H), 4.05 (d, 2H, J=12.3), 3.85 (d, 2H, J=7.2), 2.83 (bs, 2H), 2.75 (m, 2H), 2.44 (d, 2H, J=6.0), 1.80 (m, 2H), 1.20 (m, 2H), 0.69 (m, 1H), 0.53 (m, 1H), 0.29 (m, 1H).

LRMS ESI (M+H$^+$) 540.29.

HPLC: 40-95% MeOH in water over 10 minutes, 16 minutes total (room temperature). Retention time=11.05 min.

Example 2

4-{3-[6-Amino-9-(5-cyclopropylcarbamoyl-3,4-dihydroxy-tetrahydro-furan-2-yl)-9H-purin-2-yl]-prop-2-ynyl}-piperidine-1-carboxylic acid cyclobutylmethyl ester

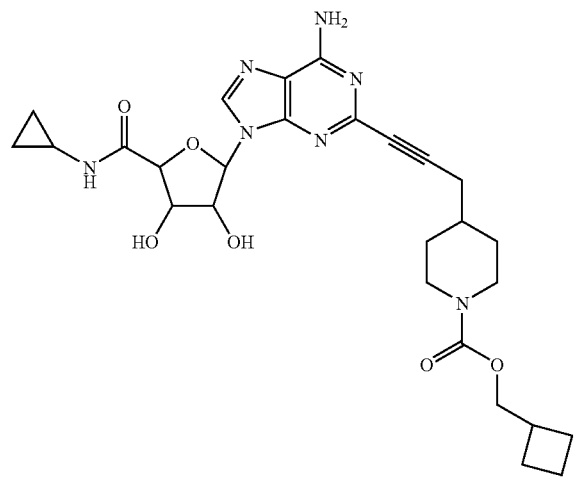

Example 2 was prepared by the method of Example 1. The compound was purified by preparative HPLC to obtain an off white solid (21% yield).

$^1$H NMR (DDMSO) δ 8.57 (s, 1H), 8.30 (s, 1H), 7.52 (s, 2H), 5.97 (d, 1H, J=6.6), 5.68 (dd, 2H, J=18.6, 5.1), 4.64 (d, 1H, J=5.1), 4.31 (d, 1H, i=1.8), 4.21 (m, 1H), 3.98 (m, 4H), 2.82 (bs, 2H), 2.72 (m, 2H), 2.43 (d, 2H, J=6.3), 2.03 (m, 2H), 1.79 (m, 4H), 1.21 (m, 2H), 0.69 (m, 1H), 0.52 (m, 1H).

LRMS ESI (M+H$^+$) 554.35.

HPLC rt=11.48 min (16 min method).

Cell culture and membrane preparation. Sf9 cells were cultured in Grace's medium supplemented with 10% fetal bovine serum, 2.5 μg/ml amphotericin B and 50 μg/ml gentamycin in an atmosphere of 50% $N_2$/50% $O_2$-Viral infection was performed at a density of $2.5\times10^6$ cells/mL with a multiplicity of infection of two for each virus used. Infected cells were harvested 3 days post-infection and washed twice in insect PBS (PBS pH 6.3). Cells were then resuspended in lysis buffer (20 mM HEPES pH 7.5, 150 mM NaCl, 3 mM $MgCl_2$, 1 mM β-mercaptoethanol (BME), 5 μg/mL leupeptin, 5 g/mL pepstatin A, 1 μg/mL aprotinin, and 0.1 mM PMSF) and snap frozen for storage at −80° C. Cells were thawed on ice, brought to 30 mL total volume in lysis buffer, and burst by $N_2$ cavitation (600 psi for 20 minutes). A low-speed centrifugation was performed to remove any unlysed cells (1000×g for 10 minutes), followed by a high-speed centrifugation (17,000×g for 30 minutes). The pellet from the final centrifugation was homogenized in buffer containing 20 mM HEPES pH 8, 100 mM NaCl, 1% glycerol, 2 μg/mL leupeptin, 2 μg/mL pepstatin A, 2 μg/mL Aprotinin, 0.1 mM PMSF, and 10 μM GDP using a small glass homogenizer followed by passage through a 26 gauge needle. Membranes were aliquoted, snap frozen in liquid $N_2$, and stored at −80° C. Membranes from cells stably expressing the human $A_1$ AR (CHO K1 cells) or $A_3$ AR (HEK 293 cells) were prepared as described (Robeva et al., 1996).

Radioligand Binding Assays. Radioligand binding to recombinant human $A_{2A}$ receptors in Sf9 cell membranes was performed using either the radiolabeled agonist, $^{125}$I-APE (Luthin et al., 1995) or the radiolabeled antagonist, $^{125}$I-ZM241385 ($^{125}$I-ZM). To detect the high affinity, GTPγS-sensitive state of $A_1$ and $A_3$ AR, we used the agonist, $^{125}$I-ABA (Linden et al., 1985; Linden et al., 1993). Binding experiments were performed in triplicate with 5 μg ($A_{2A}$) or 25 μg ($A_1$ and $A_3$) membrane protein in a total volume of 0.1 mL HE buffer (20 mM HEPES and 1 mM EDTA) with 1 U/mL adenosine deaminase and 5 mM $MgCl_2$ with or without 50 μM GTPγS. Membranes were incubated with radioligands at room temperature for three hours (for agonists) or two hours (for antagonists) in Millipore Multiscreen® 96-well GF/C filter plates and assays were terminated by rapid filtration on a cell harvester (Brandel, Gaithersburg, Md.) followed by 4×150 μl washes over 30 seconds with ice cold 10 mM Tris-HCl, pH 7.4, 10 mM $MgCl_2$. Nonspecific binding was measured in the presence of 50 μM NECA. Competition binding assays were performed as described (Robeva et al., 1996) using 0.5-1 nM $^{125}$I-APE, $^{125}$I-ZM241385, or $^{125}$I-ABA. Changing pipette tips following each serial dilution to prevent transfer on tips of potent hydrophobic compounds. The $K_i$ values for competing compound binding to a single site were derived from $IC_{50}$ values with correction for radioligand and competing compound depletion as described previously (Linden, 1982).

Linden J (1982) Calculating the Dissociation Constant of an Unlabeled Compound From the Concentration Required to Displace Radiolabel Binding by 50%. *J Cycl Nucl Res* 8: 163-172.

Linden J, Patel A and Sadek S (1985) [$^{125}$I]Aminobenzyladenosine, a New Radioligand With Improved Specific Binding to Adenosine Receptors in Heart. *Circ Res* 56: 279-284.

Linden J, Taylor H E, Robeva A S, Tucker A L, Stehle J H, Rivkees S A, Fink J S and Reppert S M (1993) Molecular Cloning and Functional Expression of a Sheep $A_3$ Adenosine Receptor With Widespread Tissue Distribution. *Mol Pharmacol* 44: 524-532.

Luthin D R, Olsson R A, Thompson R D, Sawmiller D R and Linden J (1995) Characterization of Two Affinity States of Adenosine $A_{2A}$ Receptors With a New Radioligand, 2-[2-(4-Amino-3-[$^{125}$I]Iodophenyl)Ethylamino]Adenosine. *Mol Pharmacol* 47: 307-313.

Robeva A S, Woodard R, Luthin D R, Taylor H E and Linden J (1996) Double Tagging Recombinant $A_1$- and $A_{2A}$- Adenosine Receptors With Hexahistidine and the FLAG Epitope. Development of an Efficient Generic Protein Purification Procedure. *Biochem Pharmacol* 51: 545-555.

Chemiluminescence Methods: Luminol enhanced chemiluminescence, a measure of neutrophil oxidative activity, is dependent upon both superoxide production and mobilization of the granule enzyme myeloperoxidase. The light is emitted from unstable high-energy oxygen species such as hypochlorous acid and singlet oxygen generated by activated neutrophils.

Purified human neutrophils (2×106/ml) suspended in Hanks balanced salt solution containing 0.1% human serum albumin (HA), adenosine deaminase (1 U/mL) and rolipram (100 nM) were incubated (37 C) in a water bath for 15 min with or without rhTNF (10 U/ml). Following incubation 100 L aliquots of the PMN were transferred to wells (White walled clear bottom 96 well tissue culture plates Costar #3670; 2 wells/condition) containing 501 HA and luminol (final concentration 100M) with or without adenosine agonist (final agonist concentrations 0.01-1000 nM). The plate was incubated 5 min (37 C) and then fMLP (50 1 in HA; final concentration IM) was added to all wells.

Peak chemiluminescence was determined with a Victor 1420 Multilabel Counter in the chemiluminescence mode using the Wallac Workstation software. Data are presented as peak chemiluminescence as percent of activity in the absence of an adenosine agonist. The EC50 was determined using PRISM software. All compounds were tested with PMNs from three separate donors.

Effect of $A_{2A}$ Agonists on Neutrophil Oxidative Activity: f-met-leu-phe (fMLP), luminol, superoxide dismutase, cytochrome C, fibrinogen, adenosine deaminase, and trypan blue were obtained from Sigma Chemical. Ficoll-hypaque was purchased from ICN (Aurora, Ohio), and Cardinal Scientific (Santa Fe, N. Mex.) and Accurate Chemicals and Scientific (Westerbury, N.Y.). Endotoxin (lipopolysaccharide; *E. coli* K235) was from List Biologicals (Campbell, Calif.). Hanks balanced salt solution (HBSS), and limulus amebocyte lysate assay kit were from BioWittaker (Walkersville, Md.). Human serum albumin (HSA) was from Cutter Biological (Elkhart, 1N). Recombinant human tumor necrosis factor-α was supplied by Dianippon Pharmaceutical Co. Ltd. (Osaka, Japan). ZM241385 (4-(2-[7-amino-2-(2-furyl)[1,2,4]triazolo[2,3-a][1,3,5]triazin-5-yl amino]ethyl)phenol) was a gift from Simon Poucher, Zeneca Pharmaceuticals, Cheshire, UK. Stock solutions (1 mM and 10 mM in DMSO) were made and stored at −20° C.

Human neutrophil preparation: Purified neutrophils (98% neutrophils and >95% viable by trypan blue exclusion) containing <1 platelet per 5 neutrophils and <50 pg/ml endotoxin (limulus amebocyte lysate assay) were obtained from normal heparinized (10 U/ml) venous blood by a one step Ficoll-hypaque separation procedure (A. Ferrante et al., *J. Immunol. Meth.*, 36, 109 (1980)).

Release of inflammatory reactive oxygen species from primed and stimulated human neutrophils Chemiluminescence: Luminol-enhanced chemiluminescence, a measure of neutrophil oxidative activity, is dependent upon both superoxide production and mobilization of the lysosomal granule enzyme myeloperoxidase. The light is emitted from unstable high-energy oxygen species generated by activated neutrophils. Purified neutrophils (5-10×10$^5$/ml) were incubated in Hanks balanced salt solution containing 0.1% human serum albumin (1 ml) with the tested $A_{2A}$ agonist with or without rolipram and with or without tumor necrosis factor α; (1 U/ml) for 30 minutes at 37° C. in a shaking water bath. Then luminol (1×10$^{-4}$ M) enhanced f-met-leu-phe (1 mcM) stimulated chemiluminescence was read with a Chronolog® Photometer (Crono-log Corp., Havertown, Pa.) at 37° C. for 2-4 minutes. Chemiluminescence is reported as relative peak light emitted (=height of the curve) compared to samples with tumor necrosis factor-α and without agonist or rolipram.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I or a stereoisomer or pharmaceutically acceptable salt thereof:

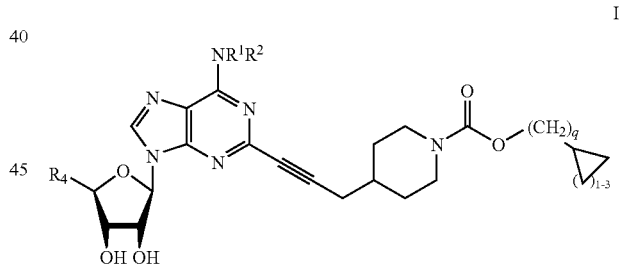

I wherein:

$R^1$ and $R^2$ independently are selected from H and $C_{1-3}$ alkyl;

$R^4$ is selected from $CH_2OR$ and $C(O)NRR$;

each R independently is selected from H, $C_{1-4}$ alkyl, cyclobutyl, and $(CH_2)_a$cyclopropyl;

a is selected from 0, 1, and 2;

q is selected from 1, 2, and 3.

2. A compound of claim 1, wherein:

$R^1$ and $R^2$ are H;

$R^4$ is C(O)NRR;

each R independently is selected from H, $C_{1-4}$ alkyl, cyclopropyl, cyclobutyl, and —$CH_2$-cyclopropyl;

q is 1.

3. A compound of claim 1, wherein the compound is:

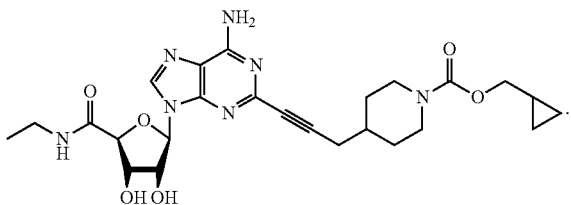

4. A compound of claim 1, wherein the compound is:

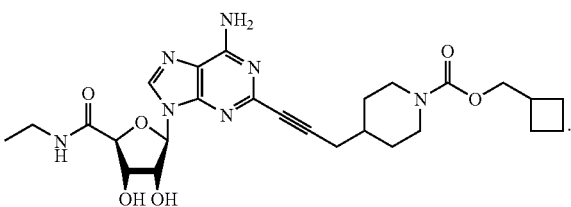

5. A compound of claim 1, wherein the compound is:

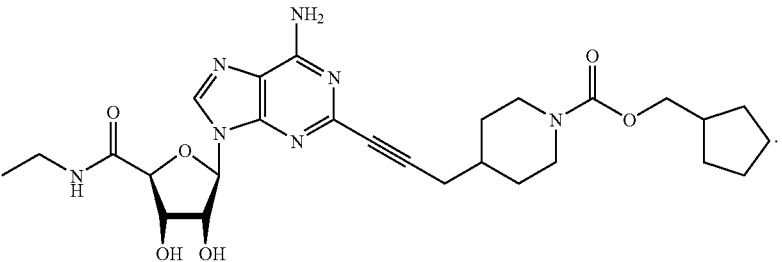

6. A compound of claim 1, wherein the compound is:

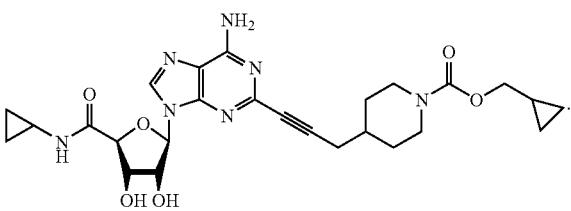

7. A compound of claim 1, wherein the compound is:

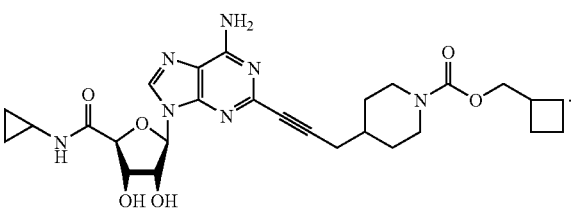

8. A compound of claim 1, wherein the compound is:

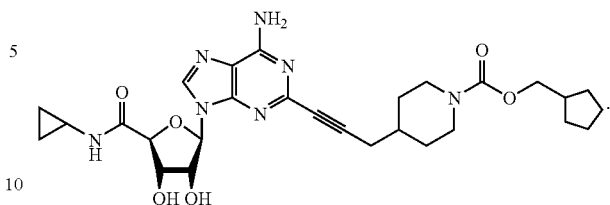

9. A pharmaceutical composition comprising a compound of claim 1 and a pharmaceutically acceptable carrier.

10. A pharmaceutical composition comprising a compound of claim 2 and a pharmaceutically acceptable carrier.

11. A pharmaceutical composition comprising a compound of claim 3 and a pharmaceutically acceptable carrier.

12. A pharmaceutical composition comprising a compound of claim 4 and a pharmaceutically acceptable carrier.

13. A pharmaceutical composition comprising a compound of claim 5 and a pharmaceutically acceptable carrier.

14. A pharmaceutical composition comprising a compound of claim 6 and a pharmaceutically acceptable carrier.

15. A pharmaceutical composition comprising a compound of claim 7 and a pharmaceutically acceptable carrier.

16. A pharmaceutical composition comprising a compound of claim 8 and a pharmaceutically acceptable carrier.

17. A method for treating a pathological condition or symptom in a subject, wherein the activity of $A_{2A}$ adenosine receptors is implicated and agonism of such activity is desired, comprising administering to the subject an effective amount of a compound of claim 1.

18. The method of claim 17, wherein the pathological condition or symptom is caused by autoimmune stimulation (autoimmune diseases), inflammation, allergic diseases, skin diseases, infectious diseases, wasting diseases, organ transplantation, tissue or cell transplantation, open wounds, adverse effects from drug therapy, a cardiovascular condition, ischemia-reperfusion injury, dialysis, gout, chemical trauma, thermal trauma, diabetic nephropathy, sickle cell disease, laminitis, and founder's disease.

19. A method to diagnose myocardial perfusion abnormalities in a mammal comprising: (a) parenterally administering to said mammal an amount of a compound of claim 1; and (b) performing a technique on said mammal to detect the presence of coronary artery stenoses, assess the severity of coronary artery stenoses or both.

* * * * *